(12) United States Patent
Dang et al.

(10) Patent No.: US 9,082,554 B2
(45) Date of Patent: Jul. 14, 2015

(54) BIOLOGICALLY SELF-ASSEMBLED NANOTUBES

(71) Applicant: Massachusetts Institute of Technology, Cambridge, MA (US)

(72) Inventors: Xiangnan Dang, Cambridge, MA (US); Hyunjung Yi, Cambridge, MA (US); Angela M. Belcher, Lexington, MA (US); Paula T. Hammond, Newton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 18 days.

(21) Appl. No.: 13/914,253

(22) Filed: Jun. 10, 2013

(65) Prior Publication Data

US 2014/0000688 A1  Jan. 2, 2014

Related U.S. Application Data

(62) Division of application No. 13/044,748, filed on Mar. 10, 2011, now Pat. No. 8,470,611.

(51) Int. Cl.

| | |
|---|---|
| *H01G 9/20* | (2006.01) |
| *B82Y 30/00* | (2011.01) |
| *B82Y 40/00* | (2011.01) |
| *H01L 51/00* | (2006.01) |
| *H01L 51/42* | (2006.01) |
| *C01B 31/02* | (2006.01) |
| *B82Y 10/00* | (2011.01) |

(52) U.S. Cl.
CPC .............. *H01G 9/2059* (2013.01); *B82Y 10/00* (2013.01); *B82Y 30/00* (2013.01); *B82Y 40/00* (2013.01); *C01B 31/0273* (2013.01); *H01L 51/0049* (2013.01); *H01L 51/0093* (2013.01); *H01L 51/426* (2013.01); *C12N 2795/14131* (2013.01); *Y02E 10/542* (2013.01); *Y02E 10/549* (2013.01)

(58) Field of Classification Search
USPC .......... 438/1, 95, 98; 977/840, 842, 894, 895; 257/E21.002, E21.536
See application file for complete search history.

(56) References Cited

U.S. PATENT DOCUMENTS

| | | | |
|---|---|---|---|
| 7,223,611 B2 * | 5/2007 | Kornilovich et al. .............. 438/3 |
| 7,332,321 B2 | 2/2008 | Belcher et al. | |
| 7,923,109 B2 | 4/2011 | Belcher et al. | |
| 8,294,135 B2 * | 10/2012 | Lebedev et al. .................. 257/9 |
| 2003/0113714 A1 | 6/2003 | Belcher et al. | |
| 2005/0221083 A1 | 10/2005 | Belcher et al. | |
| 2005/0224360 A1 | 10/2005 | Varghese et al. | |
| 2006/0121346 A1 | 6/2006 | Nam et al. | |
| 2006/0137741 A1 | 6/2006 | Park et al. | |
| 2006/0172282 A1 | 8/2006 | Naik et al. | |
| 2007/0051941 A1 | 3/2007 | Duerr et al. | |
| 2007/0285843 A1 | 12/2007 | Tran | |
| 2009/0220561 A1 | 9/2009 | Jin et al. | |
| 2010/0040862 A1 | 2/2010 | Shiba et al. | |
| 2010/0093562 A1 | 4/2010 | Culver et al. | |

(Continued)

OTHER PUBLICATIONS

International Preliminary Report on Patentability dated Sep. 19, 2013 for PCT/US2011/027831.

(Continued)

*Primary Examiner* — Mohsen Ahmadi
(74) *Attorney, Agent, or Firm* — Foley & Lardner LLP

(57) ABSTRACT

A method of a general biological approach to synthesizing compact nanotubes using a biological template is described.

5 Claims, 11 Drawing Sheets

(56) References Cited

U.S. PATENT DOCUMENTS

2010/0120236 A1* 5/2010 Saraf et al. .................... 438/492
2010/0291224 A1 11/2010 Tong et al.
2011/0116993 A1 5/2011 Nam et al.

OTHER PUBLICATIONS

Arnold, M. S. et al. "Sorting carbon nanotubes by electronic structure using density differentiation." *Nature Nanotech.* 1, 60-65 (2006).
Barone, P. W., et al., Near-infrared optical sensors based on single-walled carbon nanotubes. *Nature Mater.* 4, 86-92 (2005).
Bonaccorso, F. Debundling and selective enrichment of SWNTs for applications in dye-sensitized solar cells. *Int. J. Photoenergy* 2010, 727134 (2010).
Brown, P., et al., Single-walled carbon nanotube scaffolds for dye-sensitized solar cells. *J. Phys. Chem. C* 112, 4776-4782 (2008).
C. Mao, C. E. Flynn, A. Hayhurst, R. Sweeney, J. Qi, G. Georgiou, B. Iverson, and A. M. Belcher, "Viral assembly of oriented quantum dot nanowires," *Proc Natl Acad Sci U S A*, vol. 100, No. 12 (2003) pp. 6946-6951.
Chen, C.-Y. et al. Highly efficient light-harvesting ruthenium sensitizer for thin-film dye-sensitized solar cells. *ACS Nano* 3, 3103-3109 (2009).
Chen, X., & Mao, S. S., Titanium dioxide nanomaterials: synthesis, properties, modifications, and applications. *Chem. Rev..* 107, 2891-2959 (2007).
Cherepy, N. J., Smestad, G. P., Grätzel, M. & Zhang, J. Z. Ultrafast electron injection: implications for a photoelectrochemical cell utilizing an anthocyanin dye-sensitized $TiO_2$ nanocrystalline electrode. *J. Phys. Chem. B* 101, 9342-9351 (1997).
Dresselhaus, M. S., et al., Raman spectroscopy of carbon nanotubes. *Physics Reports* 409, 47-99 (2005).
Eder, D. & Windle, A. H. Carbon—inorganic hybrid materials: the carbon-nanotube/$TiO_2$ interface. *Adv. Mater.* 20, 1787-1793 (2008).
Geng, J. et al. Effect of SWNT defects on the electron transfer properties in P3HT/SWNT hybrid materials. *Adv. Funct. Mater.* 18, 2659-2665 (2008).
Halme, J., et al., Device physics of dye solar cells. *Adv. Mater.* 22, E210-E234 (2010).
Han, J.-H. et al. Exciton antennas and concentrators from core-shell and corrugated carbon nanotube filaments of homogeneous composition. *Nature Mater.* 9, 833-839 (2010).
Hone, J., et al., Thermal conductivity of single-walled carbon nanotubes. *Physical Review B* 59, R2514 (1999).
Jang, S.-R., et al., Incorporation of functionalized single-wall carbon nanotubes in dye-sensitized $TiO_2$ solar cells. *Langmuir* 20, 9807-9810 (2004).
K. T. Nam, D.W. Kim, P.J. Yoo, C.-Y. Chiang, N. Meethong, P.T. Hammond, Y.-M. Chiang, A.M. Belcher, "Virus enabled synthesis and assembly of nanowires for lithium ion battery electrodes," *Science*, vol. 312, No. 5775 (2006) pp. 885-888.
Kamat, P. V. Quantum dot solar cells: Semiconductor nanocrystals as light harvesters. *J. Phys. Chem. C* 112, 18737-18753 (2008).
Kongkanand, A. et al. Quantum dot solar cells. tuning photoresponse through size and shape control of CdSe—$TiO_2$ architecture. *J. Am. Chem. Soc.* 130, 4007-4015 (2008).
Kongkanand, A., et al., Single wall carbon nanotube scaffolds for photoelectrochemical solar cells. capture and transport of photogenerated electrons. *Nano Lett.* 7, 676-680 (2007).
Law, M. et al. Nanowire dye-sensitized solar cells. *Nature Mater.* 4, 455-459 (2005).
Lee, K.-M., et al., Incorporating carbon nanotube in a low-temperature fabrication process for dye-sensitized $TiO_2$ solar cells. *Sol. Energy Mater. Sol. Cells* 92, 1628-1633 (2008).
Lee, S.-K., et al., Cobalt ion mediated self-assembly of genetically engineered bacteriophage for biomimetic Co—Pt hybrid material. *Biomacromolecules* 7, 14-17 (2005).
Lee, S.-W., et al., Ordering of quantum dots using genetically engineered viruses. *Science* 296, 892-895 (2002).
Lee, Y. J. et al. Fabricating genetically engineered high-power lithium-ion batteries using multiple virus genes. *Science* 324, 1051-1055 (2009).
Mora-Seró, I. & Bisquert, J. Breakthroughs in the development of semiconductor-sensitized solar cells. *J. Phys. Chem. Lett.* 1, 3046-3052 (2010).
Mora-Seró, I. et al. Recombination in quantum dot sensitized solar sells. *Acc. Chem. Res.* 42, 1848-1857 (2009).
Nazeeruddin, M. K. et al. Combined experimental and DFT-TDDFT computational study of photoelectrochemical cell ruthenium sensitizers. *J. Am. Chem. Soc.* 127, 16835-16847 (2005).
Nazeeruddin, M. K. et al. Conversion of light to electricity by cis-$X_2$bis(2,2'-bipyridyl-4,4'-dicarboxylate)ruthenium(II) charge-transfer sensitizers ($X=Cl^-$, $Br^-$, $I^-$, $CN^-$, and $SCN^-$) on nanocrystalline titanium dioxide electrodes. *J. Am. Chem. Soc.* 115, 6382-6390 (1993).
Ng, Y. H. et al. To what extent do graphene scaffolds improve the photovoltaic and photocatalytic response of $TiO_2$ nanostructured films? *J. Phys. Chem. Lett.* 1, 2222-2227 (2010).
O'Connell, M. J. et al. Band gap fluorescence from individual single-walled carbon nanotubes. *Science* 297, 593-596 (2002).
O'Regan, B. & Grätzel, M. A low-cost, high-efficiency solar cell based on dye-sensitized colloidal $TiO_2$ films. *Nature* 353, 737-740 (1991).
Robel, I., Kuno, M. & Kamat, P. V. Size-dependent electron injection from excited CdSe quantum dots into $TiO_2$ nanoparticles. *J. Am. Chem. Soc.* 129, 4136-4137 (2007).
Sagawa, T., Yoshikawa, S. & Imahori, H. One-dimensional nanostructured semiconducting materials for organic photovoltaics. *J. Phys. Chem. Lett.* 1, 1020-1025 (2010).
Sambur, J. B., Novet, T. & Parkinson, B. A. Multiple exciton collection in a sensitized photovoltaic system. *Science* 330, 63-66 (2010).
Sarikaya, M. et al. Molecular biomimetics: nanotechnology through biology. *Nature Mater.* 2, 577-585 (2003).
Tan, P. H. et al. Photoluminescence spectroscopy of carbon nanotube bundles: evidence for exciton energy transfer. *Phys. Rev. Lett.* 99, 137402 (2007).
Tang, Y.-B. et al. Incorporation of graphenes in nanostructured $TiO_2$ films via molecular grafting for dye-sensitized solar cell application. *ACS Nano* 4, 3482-3488 (2010).
Varghese, O. K., et al., Long vertically aligned titania nanotubes on transparent conducting oxide for highly efficient solar cells. *Nature Nanotech.* 4, 592-597 (2009).
Wang, S. et al. Peptides with selective affinity for carbon nanotubes. *Nature Mater.* 2, 196-200 (2003).
Whaley, S. R. et al. Selection of peptides with semiconductor binding specificity for directed nanocrystal assembly. *Nature* 405, 665-668 (2000).
Yang, N. et al. Two-dimensional graphene bridges enhanced photoinduced charge transport in dye-sensitized solar cells. *ACS Nano* 4, 887-894 (2010).
Zheng, M. & Diner, B. A. Solution redox chemistry of carbon nanotubes. *J. Am. Chem. Soc.* 126, 15490-15494 (2004).

* cited by examiner

BIOLOGICALLY SELF-ASSEMBLED NANOTUBES

CLAIM OF PRIORITY

This application claims priority to U.S. application Ser. No. 13/044,748, filed on Mar. 10, 2011, of which is incorporated by reference in its entirety.

TECHNICAL FIELD

This invention relates to biologically self-assembled nanotubes, and methods of making and using them.

BACKGROUND

In nature, organisms can build complex inorganic micro- and nanostructures by a process termed "biomineralization." Natural biological systems have evolved diverse structures, e.g., bones, teeth, mollusk shells and magnetosomes, which exhibit greatly increased structural integrity compared to the organic scaffold from which they are formed. Nature's design principles are very useful as they can provide new insights that allows engineers to create new inorganic nanomaterials via environmentally benign routes.

The ability of certain biomolecules to direct the growth and organization of inorganic solids has been noticed in naturally-occurring biomineralization systems (E. Baeuerlein, *Biomineralization: From Biology to Biotechnology and Medical Application*, Wiley-VCH, Weinheim, N.Y., 2000. S. Mann, *Biomineralization: Principles and Concepts in Bioinorganic Materials Chemistry*, Oxford chemistry masters, 5, Oxford University Press, Oxford, N.Y., 2001, which is incorporated by reference in its entirety). It has also been demonstrated that certain viruses can serve as a template for the synthesis of inorganic nanostructures by identifying and engineering peptide aptamers expressed on the surface of viruses (S. W. Lee, C. Mao, C. E. Flynn, and A. M. Belcher, "Ordering of quantum dots using genetically engineered viruses," *Science*, Vol. 296, No. 5569 (2002) pp. 892-895; C. Mao, C. E. Flynn, A. Hayhurst, R. Sweeney, J. Qi, G. Georgiou, B. Iverson, and A. M. Belcher, "Viral assembly of oriented quantum dot nanowires," *Proc Natl Acad Sci USA*, Vol. 100, No. 12 (2003) pp. 6946-6951, each of which is incorporated by reference in its entirety). It has also been found that two-dimensional self-assembly of viruses can be utilized to prepare unique viral thin-films that are useful in building battery electrodes via biomineralization (K. T. Nam, D. W. Kim, P. J. Yoo, C.-Y. Chiang, N. Meethong, P. T. Hammond, Y.-M. Chiang, A. M. Belcher, "Virus enabled synthesis and assembly of nanowires for lithium ion battery electrodes," *Science*, Vol. 312, No. 5775 (2006) pp. 885-888, each of which is incorporated by reference in its entirety). These relatively new technologies offer potential for further development of advanced biotechnological devices useful in the fields of renewable energy, medical technologies, electronics, optical systems, and materials.

SUMMARY

In one aspect, a method of making a composite material includes providing a composition including a virus with binding affinity to nanotubes, contacting the nanotubes to the virus, thereby forming a virus-nanotube complex, and contacting a plurality of nanoparticles to the virus-nanotube complex, thereby forming a virus-nanotube-nanoparticle complex.

The method can further include adjusting the pH of the composition to a predetermined pH, thereby dispersing the nanotubes along the virus. The virus can include a template for nucleation and growth of nanoparticles. The method can further include growing the nanoparticles of the virus-nanotube-nanoparticle complex. The method can further include removing the virus, thereby forming a nanotube-nanoparticle complex.

Contacting the nanotubes to the virus can include non-covalent binding of the nanotubes to the virus. The virus can be a genetically engineered virus. The virus can be M13.

The plurality of nanoparticles can include inorganic nanoparticles. The inorganic nanoparticles can include $TiO_2$ nanoparticles. The nanotubes can include semiconductive nanotubes. The semiconductive nanotubes can include single-walled carbon nanotubes.

In another aspect, a method of making a composite material includes providing a composition including a virus with binding affinity to carbon nanotubes, contacting the carbon nanotubes to the virus, thereby forming a virus-carbon nanotube complex, contacting a plurality of inorganic nanoparticles to the virus-carbon nanotube complex, thereby forming a virus-carbon nanotube-inorganic nanoparticle complex, growing the inorganic nanoparticles of the virus-carbon nanotube-inorganic nanoparticle complex, and removing the virus, thereby forming a carbon nanotube-inorganic nanoparticle complex.

In another aspect, a method of making a photovoltaic device includes providing a composition including a virus with binding affinity to nanotubes, contacting the nanotubes to the virus, thereby forming a virus-nanotube complex, adjusting the pH of the composition to a predetermined pH, thereby dispersing the nanotubes along the virus, contacting a plurality of nanoparticles to the virus-nanotube complex, thereby forming a virus-nanotube-nanoparticle complex, removing the virus from the virus-nanotube-nanoparticle complex, thereby forming a nanotube-nanoparticle complex; and incorporating the nanotube-nanoparticle complex into a photovoltaic device.

The virus can be a genetically engineered M13 virus. The plurality of nanoparticles can include inorganic nanoparticles. The nanotubes can include semiconductive carbon nanotubes. Incorporating the nanotube-nanoparticle complex into a photovoltaic device can include forming a photoanode with the nanotube-nanoparticle complex. The photovoltaic device can be a dye-sensitized solar cell.

Removing the virus from the virus-nanotube-nanoparticle complex can include annealing in an Ar atmosphere at a temperature of at least 600° C.

In another aspect, a photovoltaic device includes a photoanode including a nanocomposite, wherein the nanocomposite includes a plurality of nanotube-nanoparticle complexes.

The nanocomposite can be a biomineralized nanomaterial. The biomineralized nanomaterial can be a virus-templated nanomaterial. The virus can include M13. The nanotubes can include semiconductive nanotubes. The nanotubes can include single-walled carbon nanotubes. The nanoparticles can include inorganic nanoparticles. The inorganic nanoparticles can include $TiO_2$ nanoparticles.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 3c is a graph showing the dependence of the power conversion efficiency and short circuit current of DSSCs on the electronic type and the concentration of SWNTs incorporated in TiO$_2$ matrix. Virus-to-SWNT ratio of 1:5 was used for all devices.

FIG. 4d is a graph showing the dependence of power conversion efficiency and short circuit current on the degree of bundling of SWNTs controlled by virus-to-SWNT ratio.

DETAILED DESCRIPTION

Figure 1:
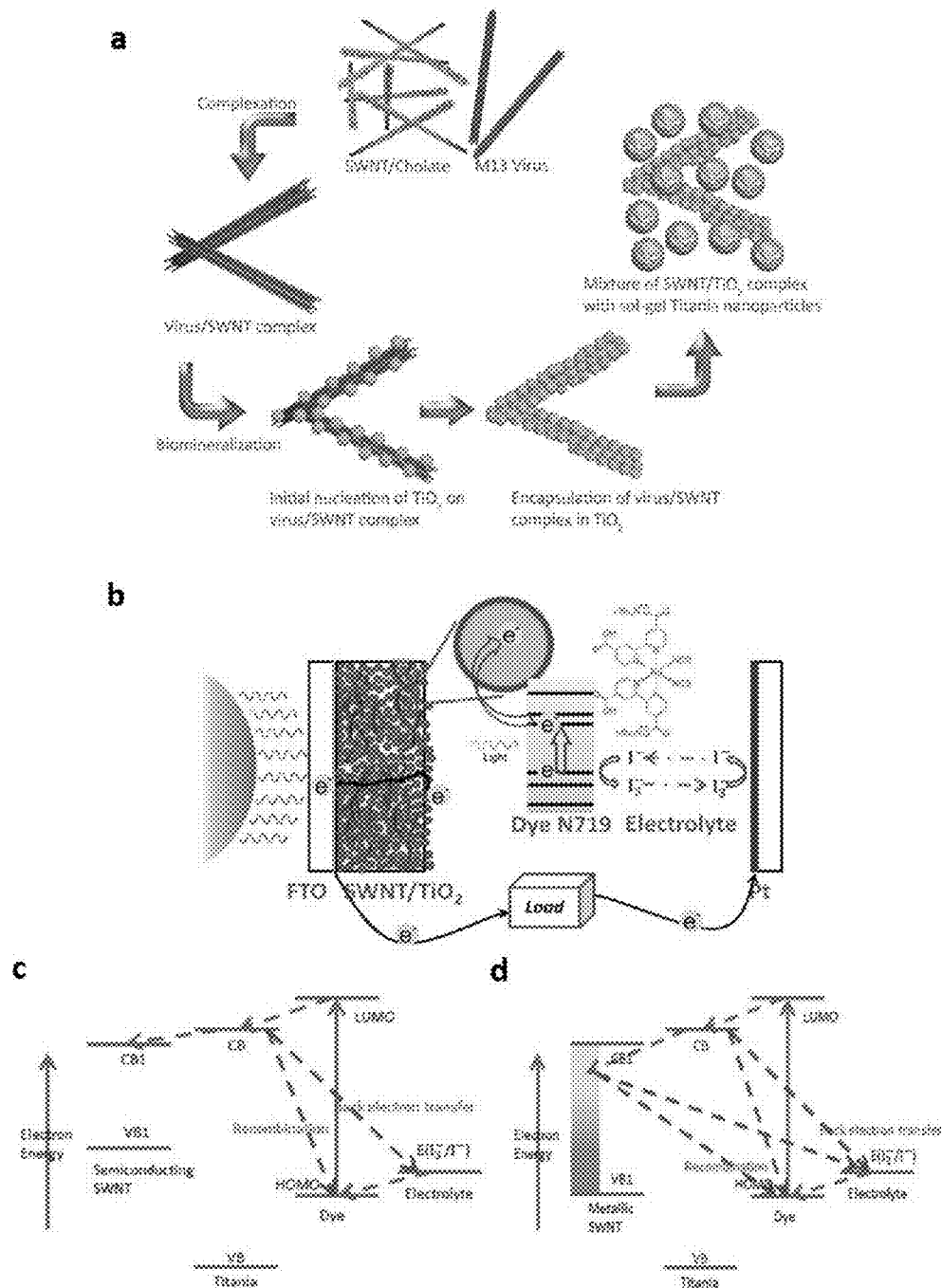
FIG. 1a is a schematic depiction of the process of virus single-walled carbon nanotube (SWNT) complexation and biomineralization of $TiO_2$ on the surface of the virus-SWNT complex.
FIG. 1b is a schematic depiction of the scheme of dye-sensitized solar cells (DSSCs) incorporated with SWNT/TiO$_2$ complex.
FIGS. 1c-d are energy diagrams of DSSCs incorporated with (c) semiconducting SWNTs and (d) metallic SWNTs.

Composite materials, such as nanocomposite materials, can provide advantageous properties that non-composite materials cannot. For example, nanocomposites including semiconducting nanotubes and photoresponsive (e.g., absorbing or emitting) materials can be useful in a variety of applications, including medical imaging (e.g., deep tissue imaging) and optoelectronic devices, such as light emitting devices and photovoltaics, e.g., dye-sensitized solar cells, quantum dot photovoltaics, and organic photovoltaics.

The need for preserving non-renewable energy and lowering carbon dioxide emission requires efficient and inexpensive approaches to utilize solar energy. Nanoporous solar cells are promising due to the low cost and potentially higher efficiency than silicon solar cells, enabled by high internal quantum efficiency, large surface-to-volume ratio, and a tunable absorption range. See, for example, Sambur, J. B., Novet, T. & Parkinson, B. A. Multiple exciton collection in a sensitized photovoltaic system. *Science* 330, 63-66 (2010); O'Regan, B. & Grätzel, M. A low-cost, high-efficiency solar cell based on dye-sensitized colloidal TiO$_2$ films. *Nature* 353, 737-740 (1991); Kamat, P. V. Quantum dot solar cells: Semiconductor nanocrystals as light harvesters. *J. Phys. Chem. C* 112, 18737-18753 (2008); and Kongkanand, A. et al. Quantum dot solar cells. tuning photoresponse through size and shape control of CdSe—TiO$_2$ architecture. *J. Am. Chem. Soc.* 130, 4007-4015 (2008), each of which is incorporated by reference in its entirety. However, in some cases fast recombination and slow carrier diffusion in nanoporous photovoltaic devices may result in low power conversion efficiency. See, for example, Mora-Seró, I. et al. Recombination in quantum dot sensitized solar sells. *Acc. Chem. Res.* 42, 1848-1857 (2009), which is incorporated by reference in its entirety. Researchers have investigated various methods to increase the power conversion efficiency of nanoporous solar cells by improving the incident photon-to-current conversion efficiency (IPCE). While increasing light absorption and charge separation efficiency have been studied widely, improving collection efficiency of photogenerated electrons has not been widely achieved. See, for example, Kamat, P. V. Quantum dot solar cells: Semiconductor nanocrystals as light harvesters. *J. Phys. Chem. C* 112, 18737-18753 (2008); Nazeeruddin, M. K. et al. Conversion of light to electricity by cis-X$_2$bis(2,2'-bipyridyl-4,4'-dicarboxylate)ruthenium(II) charge-transfer sensitizers (X=Cl$^-$, Br$^-$, I$^-$, CN$^-$, and SCN$^-$) on nanocrystalline titanium dioxide electrodes. *J. Am. Chem. Soc.* 115, 6382-6390 (1993); Chen, C.-Y. et al. Highly efficient light-harvesting ruthenium sensitizer for thin-film dye-sensitized solar cells. *ACS Nano* 3, 3103-3109 (2009); Cherepy, N. J., Smestad, G. P., Grätzel, M. & Zhang, J. Z. Ultrafast electron injection: implications for a photoelectrochemical cell utilizing an anthocyanin dye-sensitized TiO$_2$ nanocrystalline electrode. *J. Phys. Chem. B* 101, 9342-9351 (1997); Nazeeruddin, M. K. et al. Combined experimental and DFT-TDDFT computational study of photoelectrochemical cell ruthenium sensitizers. *J. Am. Chem. Soc.* 127, 16835-16847 (2005); Robel, I., Kuno, M. & Kamat, P. V. Size-dependent electron injection from excited CdSe quantum dots into TiO$_2$ nanoparticles. *J.*

*Am. Chem. Soc.* 129, 4136-4137 (2007); and Sagawa, T., Yoshikawa, S. & Imahori, H. One-dimensional nanostructured semiconducting materials for organic photovoltaics. *J. Phys. Chem. Lett.* 1, 1020-1025 (2010), each of which has been incorporated by reference in its entirety. Most of the work was devoted to developing materials with higher electron mobility and/or nanostructures with a facilitated electron path, such as vertical nanotube arrays or nanowire arrays. See, for example, Varghese, O. K., et al., Long vertically aligned titania nanotubes on transparent conducting oxide for highly efficient solar cells. *Nature Nanotech.* 4, 592-597 (2009) and Law, M. et al. Nanowire dye-sensitized solar cells. *Nature Mater.* 4, 455-459 (2005), each of which has been incorporated by reference in its entirety. Increasing electron diffusion length by changing materials or nanostructures, however, alters other important materials and device properties such as charge separation and recombination and the surface area of thin films. Thus far, a method capable of increasing electron diffusion length while keeping other essential device physics parameters unaffected is absent.

Making nanocomposites from combinations of materials each with their own unique functional advantage is an alternative way to improve electron collection. Single-walled carbon nanotubes (SWNTs) have been regarded for a long time as a promising candidate for nanocomposite photoanodes in photovoltaic devices because of their excellent electron mobility and one-dimensional shape. See, for example, Kongkanand, A., et al., Single wall carbon nanotube scaffolds for photoelectrochemical solar cells. capture and transport of photogenerated electrons. *Nano Lett.* 7, 676-680 (2007); Brown, P., et al., Single-walled carbon nanotube scaffolds for dye-sensitized solar cells. *J. Phys. Chem. C* 112, 4776-4782 (2008); and Saito, R., et al., *Physical Properties of Carbon Nanotubes.* (Imperial College Press, London, 1998), each of which is incorporated by reference in its entirety. However, no report has shown pronounced improvement in power conversion efficiency of SWNT-incorporated nanoporous solar cells. This is probably due to several different factors.

First, as-produced SWNTs are an ensemble of metallic and semiconducting SWNTs. While semiconducting SWNTs can provide an efficient electron diffusion path without recombination, metallic components provide a short-circuit path, negating any possible improvements. Moreover, the strong tendency for SWNTs to form bundles creates contact between semiconducting and metallic SWNTs, transferring electrons from semiconducting SWNTs to metallic ones. See, for example, Bonaccorso, F. Debundling and selective enrichment of SWNTs for applications in dye-sensitized solar cells. *Int. J. Photoenergy* 2010, 727134 (2010) and O'Connell, M. J. et al. Band gap fluorescence from individual single-walled carbon nanotubes. *Science* 297, 593-596 (2002), each of which is incorporated by reference in its entirety. Chemical modifications or surfactants have been used to prevent SWNT bundling, but these methods either deteriorate the electronic properties of SWNTs or make the heterogeneous nucleation of nanocrystals on SWNTs difficult. See, for example, Jang, S.-R., et al., Incorporation of functionalized single-wall carbon nanotubes in dye-sensitized $TiO_2$ solar cells. *Langmuir* 20, 9807-9810 (2004); Kongkanand, A., et al., Single wall carbon nanotube scaffolds for photoelectrochemical solar cells. capture and transport of photogenerated electrons. *Nano Lett.* 7, 676-680 (2007); Brown, P., et al., Single-walled carbon nanotube scaffolds for dye-sensitized solar cells. *J. Phys. Chem. C* 112, 4776-4782 (2008); and Geng, J. et al. Effect of SWNT defects on the electron transfer properties in P3HT/SWNT hybrid materials. *Adv. Funct. Mater.* 18, 2659-2665 (2008), each of which is incorporated by reference in its entirety. Therefore, it is desirable to develop ways to incorporate SWNTs in photovoltaic devices in a manner that takes advantage of their desirable properties more effectively.

M13 virus is a filamentous bacteriophage which can be genetically engineered to express peptides having a selective binding affinity for certain materials, e.g., inorganic materials. See, for example, Whaley, S. R. et al. Selection of peptides with semiconductor binding specificity for directed nanocrystal assembly. *Nature* 405, 665-668 (2000); Lee, S.-W., et al., Ordering of quantum dots using genetically engineered viruses. *Science* 296, 892-895 (2002); and Sarikaya, M. et al. Molecular biomimetics: nanotechnology through biology. *Nature Mater.* 2, 577-585 (2003), each of which has been incorporated by reference in its entirety.

Engineered M13 bacteriophage can serve as a template for nanoparticle growth. See, for example, Ki Tae Nam, Dong-Wan Kim, P. J. Y. *Science* 2006, 312, 885, which is incorporated by reference in its entirety. Protein engineering techniques (e.g., phage display) can produce a virus that has a protein coat with binding affinity for a desired target material, e.g., an inorganic material such as a metal or a metal oxide. The M13 coat protein can be engineered to include a metal binding motif, which, for example, can be a negatively charged motif, e.g., tetraglutamate or a peptide with a binding affinity to a metal. For example, the motif can be a 12-amino acid peptide with a high affinity for Au. In one example, engineered M13 virus particles allowed control of the assembly of nanowires of $Co_3O_4$ with a small percentage of Au dopant. Id.

M13 bacteriophage contains about 2700 copies of a major coat protein, pVIII protein, which are longitudinally assembled along the virus's DNA. The 2700 copies are stacked in units of five in a helical array. Moreover, several copies of minor coat proteins (pIII, pVI, pVII, and pIX proteins) are assembled at the two ends of the virus. This unique periodic, uniform structure is genetically controlled, and can be used to create tailor-made micro- or nanostructures. The various proteins may be genetically modified to have a specific peptide motif that can bind and organize nanomaterials. Because the amino acid sequence of this motif is genetically linked to the virus DNA and contained within the virus capsid, exact genetic copies of the virus scaffold can be created easily and quickly reproduced by infection in bacterial hosts.

In one embodiment, the major coat protein of M13 bacteriophage is genetically engineered to specifically bind to metal ions or nanoparticles. Metal oxide nanotubes can be synthesized using this engineered virus template. Due to the anisotropic structure of bacteriophage, virus-based metal oxide nanotubes can self-assemble into a mesoporous nanocrystalline form. Furthermore, the highly oriented helical major coat proteins of M13 virus promote the structural stability of individual virus-based nanotubes, and can increase the durability of devices or components incorporating them. Additional aspects of virus-templated formation of micro- and nanostructures are described in U.S. patent application Ser. No. 11/254,540, the contents of which are incorporated herein by reference.

As used herein, the term "peptide" denotes a string of at least two amino acids linked together by peptide bonds. Peptide may refer to an individual peptide or a collection of peptides. Peptides may contain only natural amino acids, although non-natural amino acids (e.g., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired activity of the peptide.

While M13 bacteriophage can have a major coat protein with a motif that binds specific metals, the motif can also block binding of other metals. For example, tetraglutamate can interact with various metal ions but blocks interaction with Au due to electrostatic repulsion. See, for example, Ki Tae Nam, Dong-Wan Kim, P. J. Y. *Science* 2006, 312, 885, which is incorporated by reference in its entirety. M13 bacteriophage can be engineered to bind to different materials at different sites, by introducing different affinity motifs in the major and minor coat proteins.

Other viruses or biomolecules can be used in place of, or in addition to, a selected virus such as the M13 virus. Alternatively or in addition, virus types which may be used for the inventive methods and compositions include, but are not limited to, tobacco mosaic virus (TMV), cowpea mosaic virus, T7 bacteriophage, T4 bacteriophage, retrovirus, adenovirus, papillomavirus, parvovirus B19, herpes simplex virus, varicella-zoster virus, cytomegalovirus, epstein-barr virus, smallpox virus, vaccinia virus, hepatitis B virus, polyoma virus, transfusion transmitted virus, enterovirus, corona virus, rhinovirus, hepatovirus, cardiovirus, aphthovirus, poliovirus, parechovirus, erbovirus, kobuvirus, teschovirus, coxsackie, reovirus, rotavirus, norwalk virus, hepatitis E virus, rubella virus, borna disease virus, dengue virus, hepatitis C virus, yellow fever virus, influenzavirus A, influenzavirus B, influenzavirus C, isavirus, thogotovirus, measles virus, mumps virus, respiratory syncytial virus, and their genetically engineered or altered versions. In various aspects, a portion of a selected virus is genetically altered such that the altered portion provides a specific binding affinity for a material of interest.

A method using a biological scaffold can be used to integrate nanotubes into photovoltaic devices for highly efficient electron collection. Importantly, this method does not significantly affect electron transfer between semiconducting nanoparticles and nanotubes nor change the pristine properties of nanotubes. Nanotubes are bound along the length of the biological scaffold and dispersed. The scaffold/nanotube complex scheme can include part of the surface of the bound nanotube exposed to water, enabling a direct contact between biomineralized nanoparticles. Moreover, biomineralized nanoparticles templated on the biological scaffold can aid the complete encapsulation of nanotubess. Nanotubes can be successfully incorporated into photoanodes of photovoltaic devices. Semiconducting nanotubes can increase power conversion efficiency of photovoltaic devices through an increased electron diffusion length, and thus a higher electron collection efficiency. With the combination of debundling of nanotubes and nanoparticles, only enabled by the biological scaffold, it can be demonstrated that semiconducting and metallic nanotubes affect device performance in opposite ways. Furthermore, bundling of nanotubes can affect photovoltaic device performance through controlling the microstructure of scaffold/nanotube complexes.

A method using an M13 virus as a biological template can be used to integrate SWNTs into photovoltaic devices for highly efficient electron collection. Importantly, this method does not significantly affect electron transfer between semiconducting nanoparticles and SWNTs nor change the pristine properties of SWNTs. SWNTs are bound along the length of the genetically engineered M13 virus and dispersed. The virus-SWNT complex scheme can include part of the surface of the bound SWNT exposed to water, enabling a direct contact between biomineralized inorganic nanocrystals and SWNTs. Moreover, biomineralized nanocrystals templated on the virus can aid the complete encapsulation of SWNTs, which is challenging to realize with surfactant-dispersed SWNTs. SWNTs can be successfully incorporated into photoanodes of dye-sensitized solar cells (DSSCs). Semiconducting SWNTs can increase power conversion efficiency of photovoltaic devices through an increased electron diffusion length, and thus a higher electron collection efficiency. With the combination of debundling of SWNTs and compact SWNT/$TiO_2$ nanocomposites, only enabled by the virus, it can be demonstrated that semiconducting and metallic SWNTs affect device performance in opposite ways. Furthermore, bundling of SWNTs can affect photovoltaic device performance through controlling the microstructure of virus-SWNT complexes.

The loaded virus, expressing one or more types of modified peptides, can be used to nucleate nanoparticles of a metal oxide. Micro- or nanoparticles and/or nanotubes can be produced at room temperature, in contrast to the elevated temperatures (>150° C.) required for some other techniques. For example, the pVIII-engineered M13 virus is incubated with a metal salt precursor, for example, cobalt chloride, at a concentration between about 1 mM and about 5 mM. Metal ions in solution are chelated by carboxylic acid groups on the pVIII proteins. Chelated metal ions are then oxidized by adding a basic solution such as sodium hydroxide (NaOH), at, for example, between about 10 mM and about 100 mM. Alternatively, metallic nanoparticles can be nucleated and grown on the virus major coat proteins by adding between about 5 mM and about 10 mM of a reducing agent such as sodium borohydride ($NaBH_4$) or hydrazine ($N_2H_2$) to a metal salt solution in which microgels are suspended. The virus can be fully coated with nanoparticles, forming a metallic nanotube. Because the metallic materials in nanostructures are very reactive, the metallic nanotube is easily oxidized in an aqueous solution or in air to produce a nanotube composed of metal oxide nanoparticles, e.g., crystalline metal oxide nanoparticles. The virus scaffold can be removed from the nanotubes, for example, using enzymes or solvents that disrupt or lyse the viral proteins without disturbing the ceramic phase.

The production conditions can be altered to modify the synthesized nanostructure. In certain embodiments, the size of the nanoparticles can vary with temperature. Smaller particles may be produced at lower temperatures while larger particles may be produced at higher temperatures. The viral system is stable from about 4° C. to about 80° C.; other templates, e.g., peptides, nucleic acids, etc., may be stable in similar, overlapping, or different temperature ranges. Particles may range in diameter from about 2 nm across to about a micron across, for example, between 2 nm and 100 nm, between 100 nm and 500 nm, or between 500 nm and 1000 nm.

Other metal oxides, such as $Mn_2O_4$ or $V_2O_5$, can be formed into micro- or nanostructures using the techniques described above. Other metals that can be used to produce micro- or nanoparticles, or nanotubes include transition metals, such as, for example, nickel, iron, cadmium, tungsten, chromium, zirconium, titanium, scandium, yttrium, copper, and others. In some embodiments, non-transition metal oxides may be formed into micro- or nanostructures. Exemplary non-transition metals that can be used include but are not limited to calcium, aluminum, barium, beryllium, magnesium, and strontium. All of these may be produced using the same engineered viruses, or biopanning may be employed to identify peptides that are even more selective for the particular metal or metal oxide. Alternatively or in addition, mixed metal oxides may be produced by incubating engineered phage in solutions including salts of more than one metal.

EXAMPLES

Preparation of Starting SWNTs

1) HiPco and CoMoCAT Solutions

Raw nanotubes (manufactured by either high-pressure carbon monoxide (HiPco) or cobalt/molybdenum oxide catalysis (CoMoCAT) processes) were obtained from Unidym (R-SWNT, batch#R0513) and Sigma-Aldrich (product#704148), respectively. Both HiPco and CoMoCAT SWNTs were first mixed with D.I. water with 2 wt % sodium cholate (SC). For HiPco SWNTs, the mixture was homogenized for 1 hour and coup-horn sonicated for 10 min at 90% amplitude while CoMoCAT SWNTs were probe-tip sonicated for 2 hours at 40% amplitude. The resulting solutions were centrifuged at 22° C. and 30,000 rpm for 4 hours to obtain individually dispersed SWNTs.

2) 99% metallic SWNTs (IsoNanotubes-M™) and 99% semiconducting SWNTs (IsoNanotubes-S™) were purchased from NanoIntegris in a solution form. The as-received SWNT solutions were dialyzed against 2 wt % SC aqueous solution before complexation with the virus.

3) (6,5)-Enriched SWNTs

Separation of (6,5)-enriched SWNTs based on density difference was performed using a modified density gradient procedure from the literature. See, for example, Han, J.-H. et al. "Exciton antennas and concentrators from core-shell and corrugated carbon nanotube filaments of homogeneous composition." *Nature Mater.* 9, 833-839 (2010) and Arnold, M. S. et al. "Sorting carbon nanotubes by electronic structure using density differentiation." *Nature Nanotech.* 1, 60-65 (2006), each of which is incorporated by reference in its entirety. CoMoCAT SWNTs in 2 wt % SC aqueous solution was first mixed with 2 wt % sodium dodecyl sulfate (SDS) solution to a final ratio of 1:4=SDS:SC. A density gradient was made using a non-ionic medium, iodixanol (OptiPrep, 60 w/v % iodixanol, Sigma-Aldrich). The concentration of initial gradient was adjusted to be 15, 20, 25 30 w/v % with a volume of 6 ml, and was positioned on top of 60 w/v % stop layer solution with a volume of 3 ml. All iodixanol layers contained 2 wt % surfactant in a ratio of 1:4=SDS:SC. Four ml of 1:4 SDS:SC SWNT solution was added on the top of the gradient, and was centrifuged at 22° C. and 32,000 rpm for 12 hours. The resulting gradient was fractionated at every 250 μl after centrifugation using a fraction recovery system (Beckman Coulter), and characterized by UV-vis-nIR absorption spectroscopy and fluorescence. Fractions enriched in the (6,5) nanotube species were collected and dialyzed against 2 wt % SC aqueous solution.

Complexation of the Virus with SWNTs

Calculated amount of SWNT-binding virus solution was mixed with the calculated volume of SWNT dispersed by 2 wt % sodium cholate (SC) in water. The mixed solution was dialyzed against water (10 mM NaCl, pH=5.3) for two days with frequent solution changes. After two days, the pH of the dialyzing solution was increased to 10. A dialysis membrane, MWCO of 12,000-14,000 (SpectraLabs.com) was used for all dialysis procedure.

Biomineralization of $TiO_2$ on the Surface of Virus-SWNT: Synthesis and Characterization Once negative charges have been induced on the surface of virus-SWNT complex, the $TiO_2$ biomineralization was completed using an alkoxide precursor. In a typical experiment, 50 μL of titanium n-butoxide (sigma Aldrich) was dissolved in 30 mL ethanol and the solution was stirred at −20° C. 10 mL aqueous solution of each different virus-SWNT complex, which was pre-cooled at 4° C., was poured into the ethanol solution under vigorously stirring (about 700 rpm). The final solution typically consists of 25% of water and 75% of ethanol. The SWNT/$TiO_2$ weight ratio is about 1/100 for virus-to-SWNT 1:5 sample, and the template/$TiO_2$ ratio was fixed when virus-to-SWNT ratio was changed to 1:2.5 or 1:10. After one hour of stirring, the precipitates were centrifuged at 3000 rpm and washed with 2 times ethanol and 2 times water, then dried in vacuum oven at room temperature overnight. The yield of biomineralized $TiO_2$ was higher than 90%. The templated nanowire morphology was observed using Transmission Electron Microscopy under 200 kV (JEOL 200CX TEM and JEOL 2010F TEM).

Fabrication of DSSCs

Synthesis of 20 nm particle sized $TiO_2$ colloid and preparation of doctor-blading paste were performed using a procedure from literature. See, for example, Chen, C.-Y. et al. Highly efficient light-harvesting ruthenium sensitizer for thin-film dye-sensitized solar cells. *ACS Nano* 3, 3103-3109 (2009), which is incorporated by reference in its entirety. The fabrication of the photoanodes of DSSCs was followed. The FTO glass (TEC15 2.2 mm thickness, 15Ω/□, Pilkington, USA) was first cleaned in a detergent solution using an ultrasonic bath for 15 min, and then rinsed with water and ethanol. After treatment in an air plasma system for 1 min, the FTO glass plates were immersed into a 40 mM aqueous $TiCl_4$ solution at 80° C. for 30 min and washed with water and ethanol. A layer of paste was coated on the FTO glass plates by doctor blading, left for 3 min to reduce the surface irregularity of the paste and then dried for 5 min at 120° C. Then the film was annealed at 500° C. for 10 min. This doctor blading procedure with paste (coating, storing, drying, and annealing) was repeated to get an appropriate thickness about 13 μm for the photoanodes. The $TiO_2$ film is treated with 40 mM $TiCl_4$ solution at 80° C. for 30 min again, rinsed with water and ethanol and then sintered at 500° C. for 30 min. After cooling down to 80° C., the $TiO_2$ electrode was immersed into a 0.5 mM N719 dye (Solaronix) in a mixture of acetonitrile and tert-butyl alcohol (volume ratio, 1:1) and kept at room temperature for 24 hours. The photoanodes incorporated with virus-SWNT complex were fabricated with modifications as following. Various amounts of SWNT/$TiO_2$ complexes (obtained by grinding thoroughly with a mortar and a pestle after biomineralization) were mixed with $TiO_2$ paste, stirred and sonicated repeatedly. Ethanol and water were removed by rotary-evaporator. The photoanodes were annealed at 600° C. in Ar gas to protect SWNTs from burning. The counter electrode was a layer of platinum about 100 nm thick sputtered on ITO substrate (Delta Technologies). The electrolyte was a solution of 0.6 M 1-butyl-3-methylimidazolium iodide (Sigma Aldrich), 0.03 M $I_2$ (Sigma Aldrich), 0.10 M guanidinium thiocyanate (Sigma Aldrich) and 0.5 M 4-tert-butyl pyridine (Sigma Aldrich) in a mixture of acetonitrile and valeronitrile (volume ratio, 85:15). The dye-adsorbed $TiO_2$ or SWNT/$TiO_2$ photoanodes and Pt counter electrodes were assembled into a sandwich type cell and sealed with a hot-melt Surlyn sealing film of 25 μm thickness (Solaronix). The size of the $TiO_2$ electrodes used was 0.16 cm$^2$ (4 mm×4 mm). The aperture of the Surlyn frame was larger than that of the TiO$_2$ area by 2 mm. Copper tape was adhered on the edge of the FTO outside of the cell. The position of the tape was 1 mm away from the edge of the Surlyn gasket and 4 mm away from the edge of the TiO$_2$ layer. Light reflection losses were eliminated using a self-adhesive fluorinated polymer film (Arktop, Asahi Glass) that also served as a 380 nm UV cut-off filter. Masks made of black plastic tape were attached on the Arktop filter.

Characterization of DSSCs: I-V Curve Measurement

Photovoltaic measurements were performed using an AM 1.5 solar simulator (Photo Emission Tech.). The power of the simulated light was calibrated to 100 mW/cm$^2$ by using a reference Si photodiode with a powermeter (1835-C, Newport) and a reference Si solar cell in order to reduce the mismatch between the simulated light and AM 1.5 (AM 1.5 stands for air mass 1.5, meaning the solar simulator used to characterize the solar cells corresponded to sunlight travelling through 1.5 atmospheres, corresponding to a solar zenith angle of 48.2°. AM 1.5 is the most used condition for characterizing power-generating panels). I-V curves were obtained by applying an external bias to the cell and measuring the generated photocurrent with a Keithley model 2400 digital source meter. The voltage step and delay time of photocurrent were 10 mV and 40 ms, respectively.

Electrochemical impedance spectra of DSSCs were measured using a Solartron 1260 frequency response analyzer. The obtained impedance spectra were fitted with the Z-view software (v3.2b, Scribner Associates Inc.). The spectra were measured at various forward bias voltages (from −0.85 to −0.45 V) in the frequency range of 0.1 Hz~1 MHz with oscillation potential amplitudes of 10 mV at room temperature. The photoanode was connected to the working electrode. The Pt electrode was connected to the auxiliary electrode and the reference electrode. The impedance measurements were carried out in dark conditions. The transmission line model is used for fitting the electrochemical impedance data.

Figure 6:
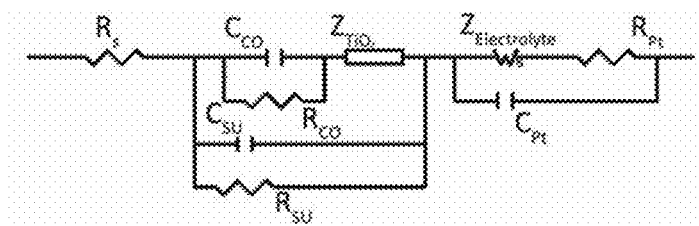
FIG. 6 is a diagram showing the transmission line model used for fitting the electrochemical impedance data.

FIG. 6 shows the transmission line model is used for fitting the electrochemical impedance data. The following are definitions of FIG. 6: $R_s$: Ohmic series resistance of the cell. $R_{CO}$ and $C_{CO}$: Contact resistance and capacitance at the interface between the conducting substrate and the TiO$_2$ photoanode film. $R_{SU}$ and $C_{SU}$: Charge transfer resistance and double layer capacitance at the substrate/electrolyte interface. $R_{Pt}$ and $C_{Pt}$: Charge transfer resistance and double layer capacitance at the counter electrode-electrolyte interface. $Z_{TiO2}$: transmission line impedance of the TiO$_2$ photoanode film consisting of the elements $r_T$ (resistivity of electron transport in the photoanode film), $r_{REC}$ (charge recombination resistance at the TiO$_2$/dye/electrolyte interface), and $c_\mu$ (chemical capacitance of the photoanode film). $Z_{electrolyte}$: mass transport impedance at the counter electrode.

During fitting the electrochemical impedance spectra to the transmission line model, the resistance and capacitance at the substrate/TiO$_2$ interface and the substrate/electrolyte interface were assumed negligible due to good contact between substrate and TiO$_2$ and blocking layer of TiO$_2$ achieved by TiCl$_4$ treatment to the substrate. Changing capacitors in the equivalent circuit model to constant phase elements (CPEs) will also improve the quality of the fitting. For detailed information about fitting electrochemical impedance spectra to the transmission line model. See, for example, Lee, S.-K., et al., Cobalt ion mediated self-assembly of genetically engineered bacteriophage for biomimetic Co—Pt hybrid material. *Biomacromolecules* 7, 14-17 (2005); Zheng, M. & Diner, B. A. Solution redox chemistry of carbon nanotubes. *J. Am. Chem. Soc.* 126, 15490-15494 (2004); and Halme, J., et al., Device physics of dye solar cells. *Adv. Mater.* 22, E210-E234 (2010), each of which is incorporated by reference in its entirety.

Complexation and Synthesis of Nanocomposites

To assemble SWNT/TiO$_2$ nanocomposites, virus-SWNT complexes were made first, and then TiO$_2$ was nucleated on the virus-SWNT complex. FIG. 1a illustrates the synthesis of virus-templated SWNT/TiO$_2$ nanocomposites. To bind and disperse SWNTs non-covalently along the length of the virus wrapped by pVIII major coat proteins, a pVIII library was constructed and viruses with binding affinity toward SWNTs were identified through a bio-panning method. See, for example, Lee, S.-K., Yun, D. S. & Belcher, A. M. Cobalt ion mediated self-assembly of genetically engineered bacteriophage for biomimetic Co—Pt hybrid material. *Biomacromolecules* 7, 14-17 (2005), which is incorporated by reference in its entirety. For the bio-panning experiment, SWNTs were prepared in a form of thin films on glass substrates to maximize the direct contact of the virus to SWNT and a constructed pVIII phage-display library was used. 10 µl of the library solution with 10$^{10}$ viruses having 2×10$^6$ different pVIII sequences were diluted with 250 µl of Tris-buffered saline (TBS, 100 mM Tris-HCl, 150 mM NaCl, pH 7.5) with different concentration of Tween-20 (TBS-T, Tween-20 concentration of 0.1-0.5 v/v %), applied to SWNT-films and incubated for 1 hour with gentle rocking. The SWNT-film was rinsed ten times with 1 ml of TBS-T to wash off unbound phage. Bound phage were eluted by 100 µl of 0.2 M Glycine-HCl, pH 2.2 and/or mid-log *E. coli* culture to harvest strongly bound virus not eluted by acid solution. The eluted phage were amplified and the same procedures were repeated for further rounds with increasing detergent concentration. After each round of panning, the numbers of eluted and amplified phage (counted as PFU) were measured using agar plates containing X-gal/isopropyl-β-D-1-thiogalactopyranoside (IPTG)/tetracycline to set the input number of phage for each round the same. Also, plaques from each round were amplified and DNA sequenced. DNA sequencing was done at MIT Biopolymers lab.

M13SK, derived from a commercially available M13KE vector (New England Biolabs. Inc.), was used for pVIII library construction. See, for example, Lee, S.-K., et al., Cobalt ion mediated self-assembly of genetically engineered bacteriophage for biomimetic Co—Pt hybrid material. *Biomacromolecules* 7, 14-17 (2005), which is incorporated by reference in its entirety. Library oligonucleotide (purchased from IDT (idtdna.com)) was designed to fuse a randomized 8-mer peptide sequence onto pVIII, and included digestion enzyme recognition sites for BamH I and Pst I. The primer and random oligonucleotides were annealed and extended to make complementary sequence of the random sequence. The extended DNA duplexes were double digested with BamHI and PstI and purified using polyacrylamide gel electrophoresis. M13SK vector was double-digested using PstI and BamHI and dephosphorylated using Antarctic phosphatase. Dephosphorylated vector was ligated with double cut-DNA duplex at 16° C. overnight and purified and concentrated. (All enzymes were purchased from New England Biolabs. Inc.) 1 µl of concentrated ligated vector was electrotransformed into XL-1 blue, electro-competent cells at 1.8 kV/cm and total 10 transformations were used for library construction. Transformed cells were incubated for 45 min and fractions of several transformants were plated on IPTG-XGal/TET agar to determine the diversity of the pVIII library while the rest were amplified. The final diversity of the pVIII library was 2×10$^6$ plaque-forming units (PFU). The relatively lower diversity of pVIII library compared to pIII library (commercially available pIII library has a diversity of ~10$^9$) is due to the more stringent requirement for virus assembly process with pVIII. In the pVIII library construction, g8 (the gene coding for pVIII), was engineered to express foreign peptide inserts. Since g8 of the virus was modified, all 2,700 copies of pVIII coat proteins expressed the peptide inserts, enabling cooperative and multivalent interaction between the surface of the virus and SWNTs.

Among several identified clones, a specific virus with the pVIII insert sequence of DSPHTELP was selected for SWNT binding and complexation for two reasons. First, it has an aromatic residue, histidine (H), which is expected to interact with the sidewall of SWNTs through π-π stacking at all pH ranges. See, for example, Wang, S. et al. Peptides with selective affinity for carbon nanotubes. *Nature Mater.* 2, 196-200 (2003), which is incorporated by reference in its entirety. Second, the $pK_a$ of the side chain of histidine is around 6 and therefore histidine in the selected sequence may allow the surface of the virus to be charge-neutralized without disrupting the virus stability. SWNTs dispersed by sodium cholate surfactants are initially negatively charged due to the cholate ions non-covalently adsorbed on the SWNTs and the virus is also negatively charged at the pH of D.I. water, (i.e., pH 6). Therefore the overall interaction between the virus and SWNT during the surfactant exchange is determined by competition between binding affinity and electrostatic repulsion. See, for example, Barone, P. W., et al., Near-infrared optical sensors based on single-walled carbon nanotubes. *Nature Mater.* 4, 86-92 (2005), which is incorporated by reference in its entirety.

Figure 7:
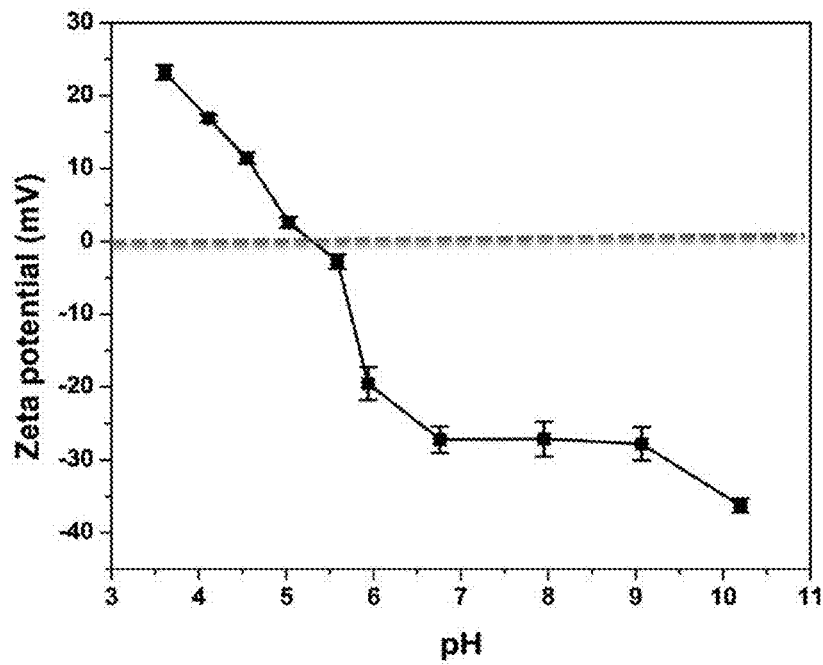
FIG. 7 is a graph showing zeta potential of the SWNT-binding virus (DSPHTELP).

To minimize the initial electrostatic repulsion between the virus and SWNT, and thus facilitating the binding of SWNT by virus, the pH of the dialyzing solution was set to the pI of the virus, 5.3 (FIG. 7). After the complexation was completed, the pH of the complex solution was increased to around 10, at which point the zeta potential of the virus becomes around −35 mV. This increased negative surface charge of the virus is advantageous for the colloidal stability of the complexes as well as for the nucleation of $TiO_2$ on the complex template. See, for example, Hiemenz, P. C. & Rajagopalan, R. *Principles of Colloid and Surface Chemistry.* (Marcel Dekker, New York, 1997), which is incorporated by reference in its entirety. The zeta potential was measured as follows. The concentration of virus (phage) solution used was $10^{12}$/ml in water with 10 mM NaCl. The stock solution of virus (~$10^{14}$/ml) was initially dissolved in 10 mM Tris, 15 mM NaCl before diluting in 10 mM NaCl in dd$H_2$O. The solution amount used to generate curve was 30 ml. The ionic concentration of the solution was as set to 10 mM NaCl for all samples to minimize the fluctuation of ionic strength during pH adjustment. The pH was then adjusted using 0.1 M NaOH until the pH was around 10. Zeta potential measurements were then made at an accumulation time of 10 with 5 measurements per sample at 20 V using DelsaNano (Beckman Coulter). Electrophoretic mobility was calculated using the Smoluchowski approximation (used for particles larger than 0.2 µm in 1 mM or greater salt solution). pH was then adjusted with 0.1 M HCl.

Figure 8:
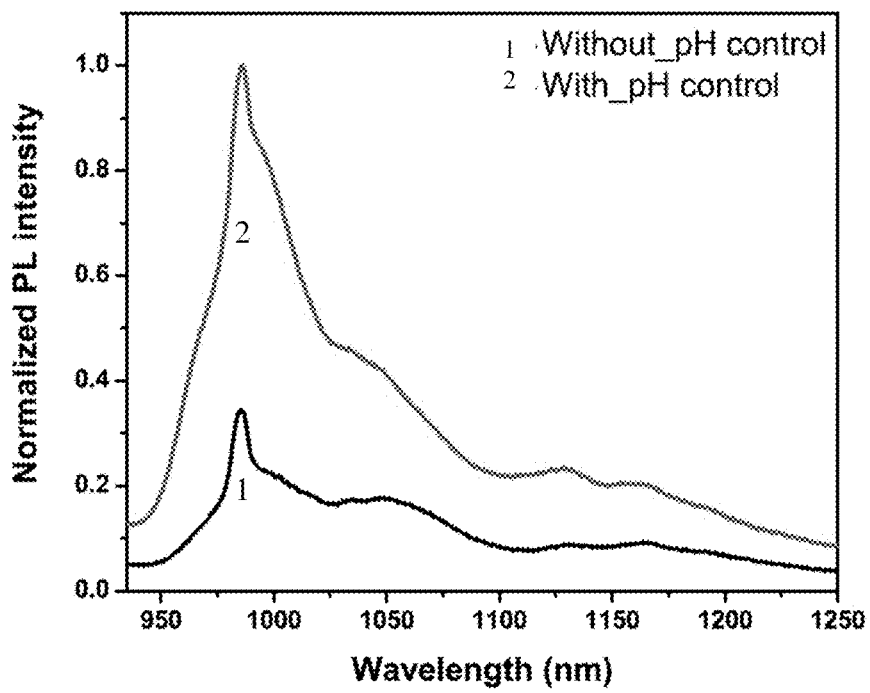
FIG. 8 is a graph showing the effect of pH-switch on complexation.

Using histidine as a pH-switch, the repulsion between the virus and the SWNT was reduced while the electrostatic repulsion between cholate-SWNTs still exists in the early stage of the complexation, minimizing possible small bundling of SWNTs. By utilizing the pH-switch, SWNTs complexed with the virus were expected to be better dispersed. The integrated photoluminescence (PL) intensity (between about 935 nm and 1,250 nm) from the virus-SWNT complex made with this pH switch increased by 2.8 times compared to the complexes made at a constant pH of 10 (FIG. 8). This implied better dispersion of SWNTs. For with pH-switch samples, the pH of the dialyzing solution was set as 5.3 (pI of the virus) and then increased to 10 after the complexation. In contrast, for the complexes without pH switch, the pH of the dialyzing solution was kept at 10 during and after the complexation. The virus-to-SWNT ratio was 1:1 for both complexes and CoMoCAT SWNTs were used for the complexation.

The virus-to-SWNT ratio was calculated as follows. The concentration of the virus was calculated using the empirical equation, $(A_{269\ nm@1\ mm} - A_{320\ nm@1\ mm}) \times 6 \times 10^{17}$/# of base pair of the viral DNA (7234)=# of viral particles/ml. The concentration of CoMoCAT was calculated using the equation, $A_{990\ nm@1\ cm} \times 13$=µg/ml. See, for example, Zheng, M. & Diner, B. A. Solution redox chemistry of carbon nanotubes. *J. Am. Chem. Soc.* 126, 15490-15494 (2004), which is incorporated by reference in its entirety. For Hipco, an empirical equation, $A_{632@1\ cm} \times 27.8$=µg/ml, was used. For 99% metallic and 99% semiconducting SWNTs, the starting concentration was 10 µg/ml (NanoIntegris). For the calculation of the number of SWNT per µg of SWNT, a value of 1 µg of SWNT=$1.06 \times 10^{12}$ was used, assuming 0.8 nm in diameter and 500 nm in length. Since different SWNT solutions had different mean length, the actual number of SWNTs can be different for various SWNTs. The mean lengths of the used SWNTs were similar to or longer than 500 nm but still shorter than 1 µm, and therefore the calculated number of SWNT could be overestimated; but by no more than a factor of 2. Accordingly, the actual virus-to-SWNT ratio of 1:5 could be less than that, but not higher than 1:2.5. Based on the data, since the device performance of the SWNT-DSSCs was not sensitive in the virus-to-SWNT ratios from 1:2.5 to 1:5, the effect of electronic type of SWNTs on device performance was still valid. For the study of the effect of the bundling, since the same SWNTs were used for the complexation, the discussion was also valid.

Figure 15:
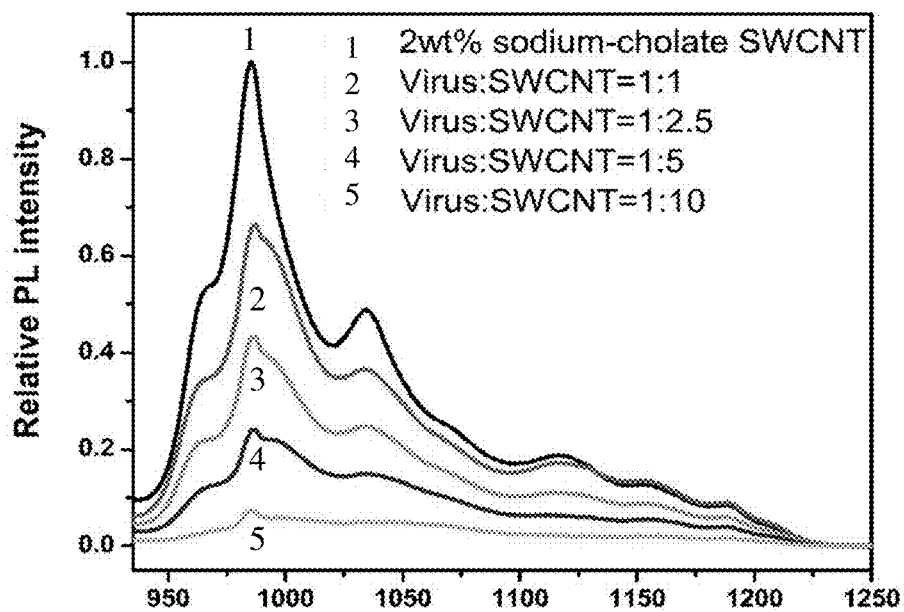
FIG. 15 is a PL spectra of virus-SWNT complex solutions with various virus-to-SWNT ratios.

Also, SWNTs stabilized by the virus through this approach retained about 82% of the integrated PL intensity of the starting SWNT solution (FIG. 15). Since metallic SWNTs in small bundles of SWNTs quench PL, higher PL intensity implied better dispersion of SWNTs. See, for example, O'Connell, M. J. et al. Band gap fluorescence from individual single-walled carbon nanotubes. *Science* 297, 593-596 (2002), which is incorporated by reference in its entirety. Therefore it can be concluded that the virus with the selected peptide sequence allowed for efficient binding and dispersion of SWNTs through pH-dependent control.

Figure 9:
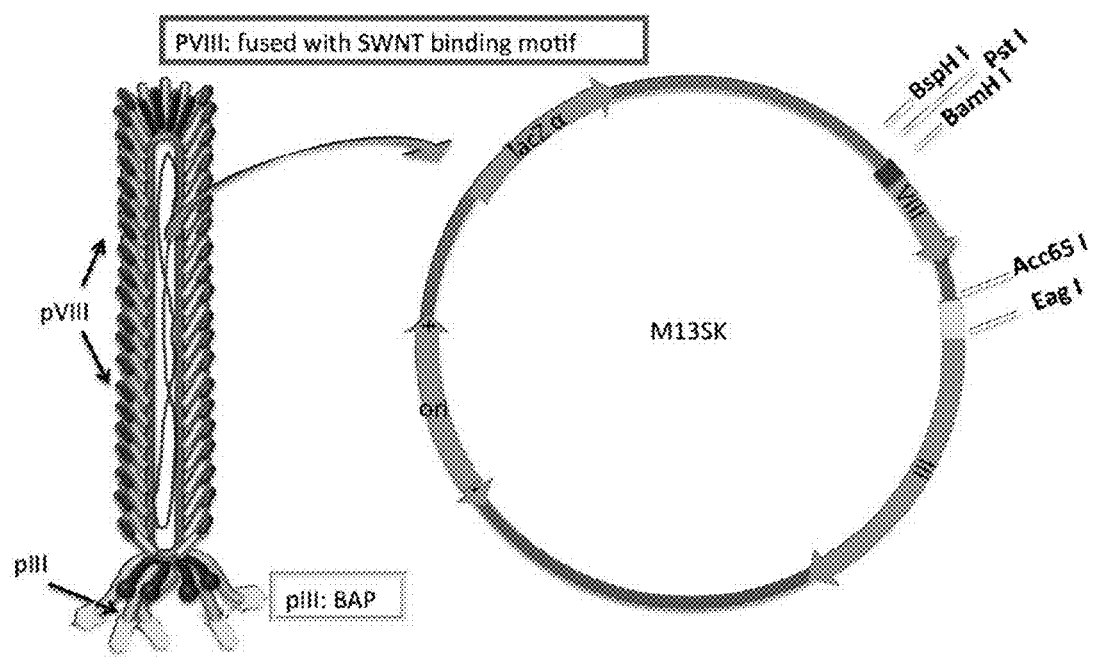
FIG. 9 is a diagrammatic scheme of an M13 virus and its cloning vector for genetic engineering.

The binding of SWNTs to the virus was confirmed using a magnetic separation method and high-resolution transmission electron microscopy (HRTEM). For HRTEM, JEOL 2010F TEM was used. For TEM analysis, virus-SWNT solutions were dropped onto Cu Quanti-foil holy grid (TedPella), washed with dd$H_2$O several times and dried. In the magnetic separation method, pIII minor coat proteins of the SWNT binding virus located at the tip of the virus were engineered to express biotin-accepting peptides and were biotinylated (FIG. 9). Biotin accepting peptide (BAP, or Avi-Tag), GLN-DIFEAQKIEWHE, identified through phage-display technique, was engineered onto pIII of SWNT-binding virus. Oligonucleotides, 5[Phos]' GTA CCT TTC TAT TCT CAC TCT GGC CTG AAC GAC ATC TTC GAG GCT CAG AAA ATC GAA TGG CAC GAG TC 3' and 5[Phos]' GGC CGA CTC GTG CCA TTC GAT TTT CTG AGC CTC GAA GAT GTC GTT CAG GCC AGA GTG AGA ATA GAA AG 3' were purchased from IDT (idtdna.com) and annealed to form a DNA duplex. The cloning vector was extracted from SWNT binding virus using standard miniprep kit (QIAGEN). The extracted vector was digested with Eag I and Acc65 I enzymes and dephosphorylated and agarose-gel purified. Purified vector and DNA duplex were ligated using T4 DNA ligase at 16° C. overnight and electrotransformed to electro-competent XL-1 blue cells. Transformed cells were incubated for 1 hr and plated and incubated at 37° C. overnight. Blue plaques were amplified and DNA sequenced to confirm the insertion of oligonucleotides to express BAP on pIII.

Figure 2:
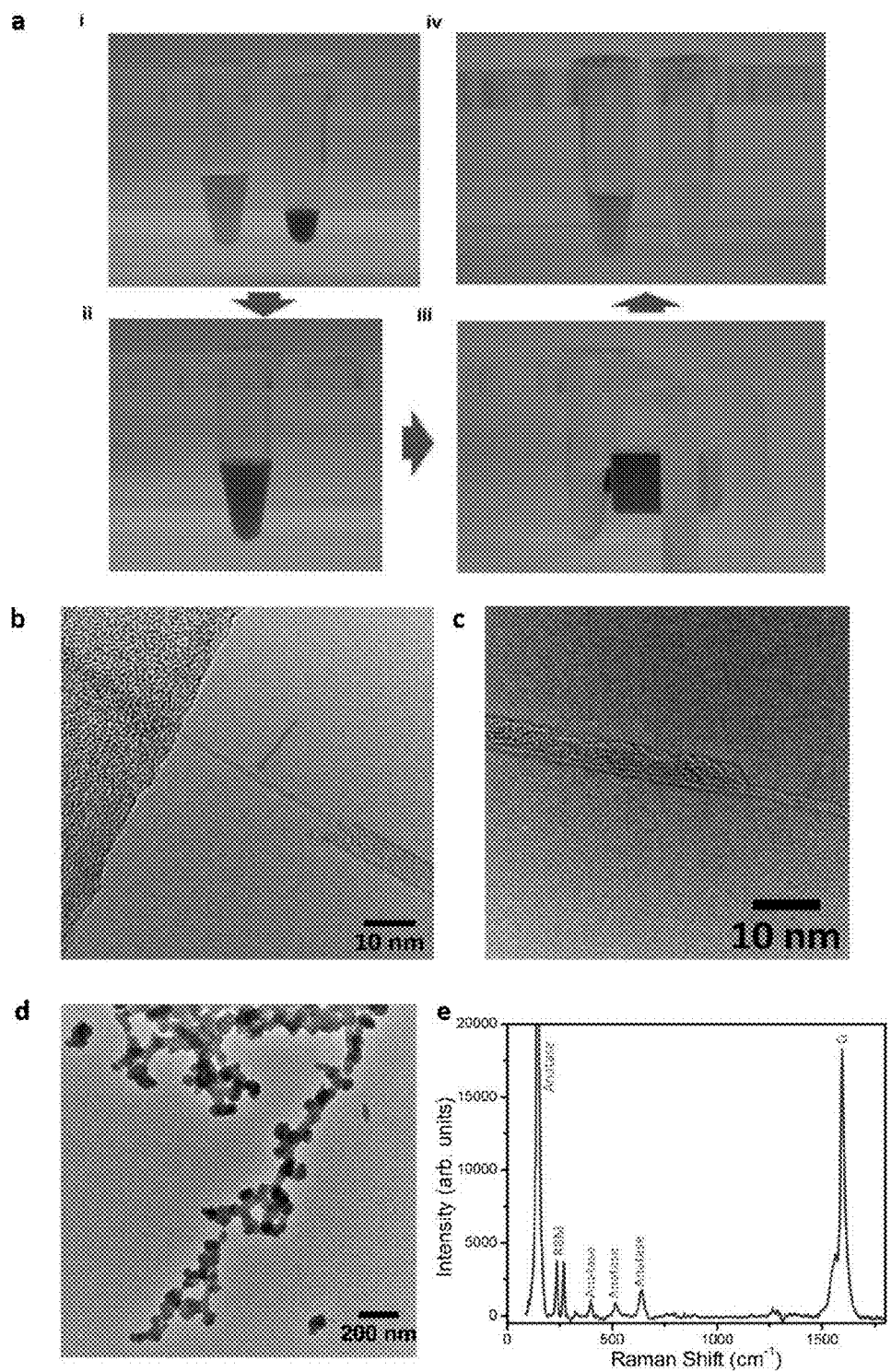
FIGS. 2Ai-iv are photographs depicting the characterization of virus-SWNT complexes. SWNT binding viruses of which p3 are enzymatically biotinylized were complexed with SWNTs (left) and combined with streptavidin-coated magnetic beads (right) and (ii) incubated. iii, Incubated solution is pulled out using magnet placed external to the eppendorf tube of the solution. iv, The supernatant is compared with the starting virus-SWNT solution, confirming binding of SWNT to the virus.
FIGS. 2b-c are HRTEM micrographs of virus-SWNT complexes. SWNTs are pointed by an arrow and the virus is indicated by dashed lines.
FIG. 2d is a TEM micrograph of TiO$_2$ biomineralized on a virus-SWNT complex.
FIG. 2e is a Raman spectrum of photoanode incorporated with SWNT/TiO$_2$ complex after being annealed in Ar at 600° C. Peaks of SWNTs and peaks of anatase are also shown.
Figure 10:
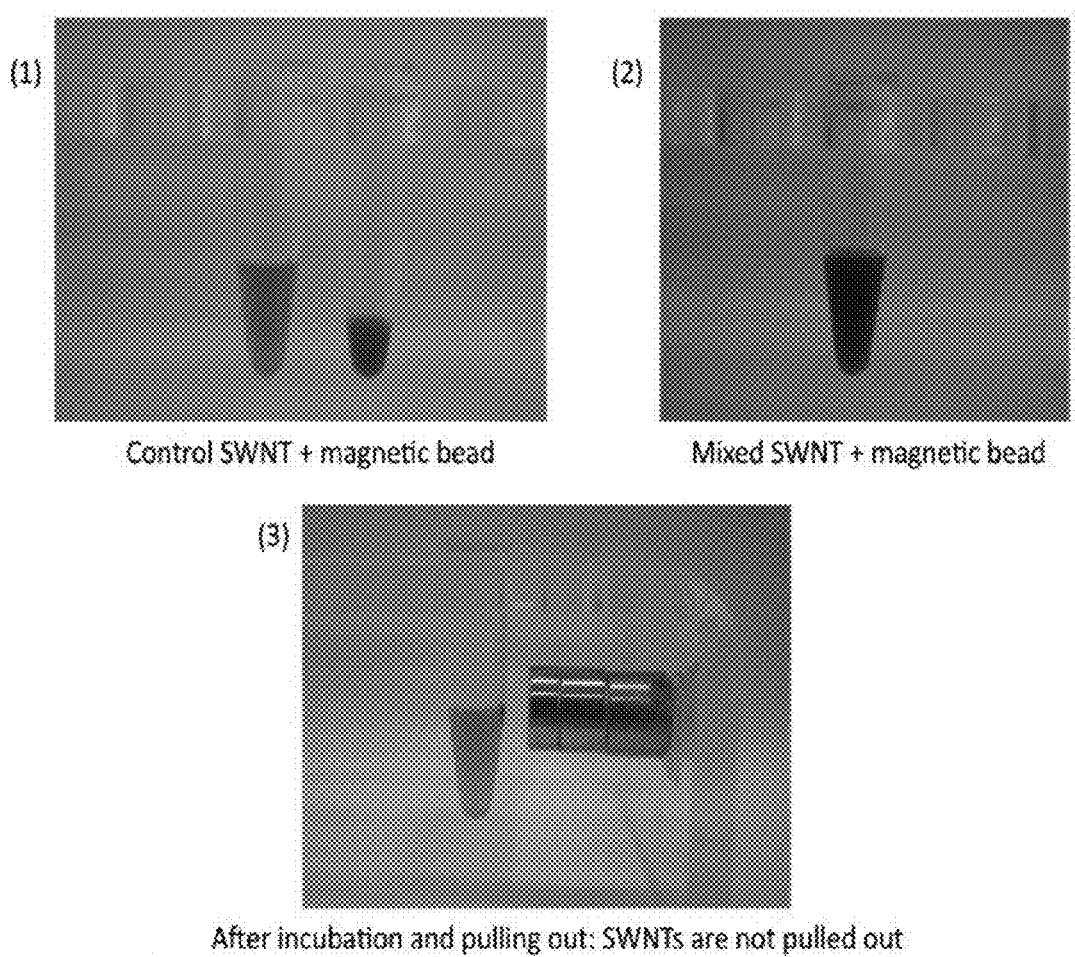
FIG. 10 are photographs showing magnetic separation of SWNTs in 2 wt % SC aqueous solution.

Biotinylated SWNT-binding viruses were complexed with SWNTs and incubated with streptavidin-coated magnetic beads. After incubation, the magnetic beads were pulled out of the solution and the remaining solution was compared with the initial virus-SWNT solution (FIG. 2a). The remaining solution was clear whereas nonspecific binding of SWNT onto the streptavidin-coated magnetic beads in a control sample was negligible (FIG. 10), implying the successful binding of SWNT on the virus. To visualize the bound SWNT along the major coat proteins of the virus, HRTEM was used (FIG. 2b,c). Part of the virus was intentionally burned off during imaging in order to clearly identify the bound SWNTs. Because part of the surface of the bound SWNTs is exposed to water, biomineralized nanocrystals on the virus can make a direct contact with SWNTs.

Figure 16:
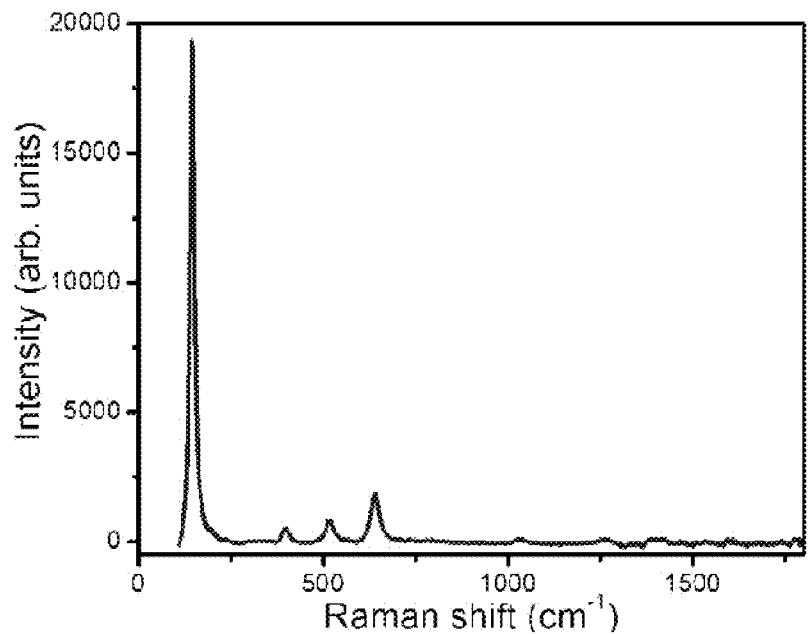
FIG. 16 is a Raman spectrum of photoanode with SWNT/TiO$_2$ complex annealed in air at 600° C.
Figure 17:
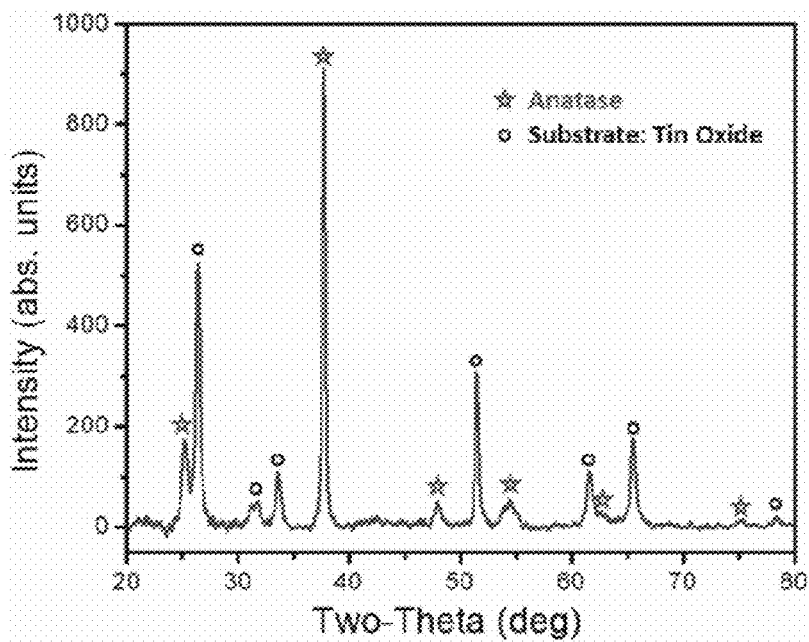
FIG. 17 is a spectra of x-ray diffraction of photoanodes with SWNT/TiO$_2$ complex annealed in Ar at 600° C. Only anatase phase of TiO$_2$ presents after annealing.

After the SWNTs were bound by the virus, nucleation of $TiO_2$ on the virus-SWNT template was optimized (typical SWNT-to-$TiO_2$ weight ratio is 1:100). Due to the fast hydrolysis of titanium alkoxide, homogeneous nucleation of $TiO_2$ dominates in aqueous solution at room temperature. See, for example, Chen, X., & Mao, S. S., Titanium dioxide nanomaterials: synthesis, properties, modifications, and applications. *Chem. Rev.* 107, 2891-2959 (2007), which is incorporated by reference in its entirety. To suppress homogeneous nucleation, $TiO_2$ was nucleated on the virus-SWNT template at lowered temperature (−20° C.) and in 75% ethanol solution. The condition was optimized so as to achieve heterogeneous nucleation and maintain the structural integrity of the virus-SWNT complex during the synthesis. In FIG. 2d, the wire-like structure in the TEM micrograph confirms the templated growth of $TiO_2$ on the virus. A Raman spectrum of the photoanode after the device fabrication shows radial breathing mode (RBM) peaks and the G peak from SWNTs, which implied the presence of a SWNT/$TiO_2$ complex (FIGS. 2e and 16). See, for example, Dresselhaus, M. S., et al., Raman spectroscopy of carbon nanotubes. *Physics Reports* 409, 47-99 (2005), which is incorporated by reference in its entirety. There was no radial breathing mode peak or G peak of SWNT in Raman spectrum when the photoanode was annealed in air at high temperature, implying the decomposition of SWNT under these conditions. Raman spectra of the final photoanode thin films were measured using a 785 nm-laser for excitation (Kaiser Optical Co.) to confirm the existence of SWNTs after the device annealing procedure. X-ray diffraction of the photoanode thin films was measured using Cu $K_\alpha$ radiation and a Rigaku RU300 powder diffractometer. The thickness of the devices was measured using profilometry (Tencor P-10 Surface Profilometer). FIG. 17 shows an X-ray diffraction pattern of the photoanode with the SWNT/$TiO_2$ complex.

Compared to other methods used to make $TiO_2$/CNT complexes, this virus enabled self-assembly method can have several advantages. See, for example, Kongkanand, A., et al., Single wall carbon nanotube scaffolds for photoelectrochemical solar cells. capture and transport of photogenerated electrons. *Nano Lett.* 7, 676-680 (2007); Brown, P., et al., Single-walled carbon nanotube scaffolds for dye-sensitized solar cells. *J. Phys. Chem. C* 112, 4776-4782 (2008); Jang, S.-R., et al., Incorporation of functionalized single-wall carbon nanotubes in dye-sensitized $TiO_2$ solar cells. *Langmuir* 20, 9807-9810 (2004); and Eder, D. & Windle, A. H. Carbon-inorganic hybrid materials: the carbon-nanotube/$TiO_2$ interface. *Adv. Mater.* 20, 1787-1793 (2008), each of which is incorporated by reference in its entirety. First, SWNTs were bound and stabilized by the virus through non-covalent binding and therefore no chemical modification of the SWNTs was needed, thus preserving the high electron mobility in the SWNTs. Moreover, the partially exposed surface of SWNT in the virus-SWNT complex enabled direct contact between SWNTs and $TiO_2$. This can be important for electron transfer at the interface of SWNT/$TiO_2$. Lastly, an excess of virus was not required to disperse SWNTs. Surfactants needed to be at a higher concentration than critical micelle concentration (CMC), typically ten to a hundred times more than the virus used for stabilizing SWNTs. The free surfactants made heterogeneous nucleation of $TiO_2$ on the surface of SWNTs difficult.

Effect of Electronic Type of SWNTs on Photovoltaic Device Performance

Figure 3:
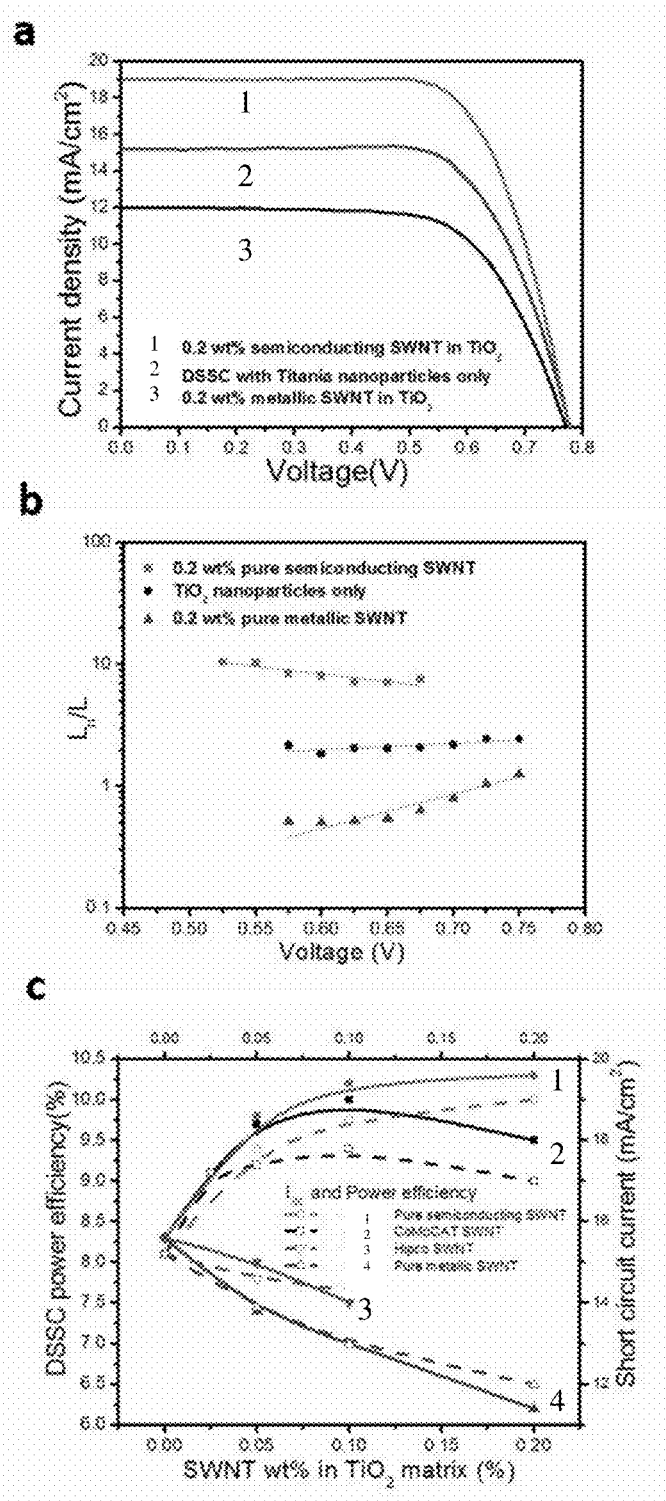
FIG. 3 are graphs of (a) I-V curves, and (b) calculated electron diffusion lengths from three DSSCs: with only TiO$_2$ nanoparticles; with 0.2 wt % pure semiconducting SWNTs; and with 0.2 wt % pure metallice SWNTs. Virus-to-SWNT ratio of 1:5 was used for all devices.
Figure 11:
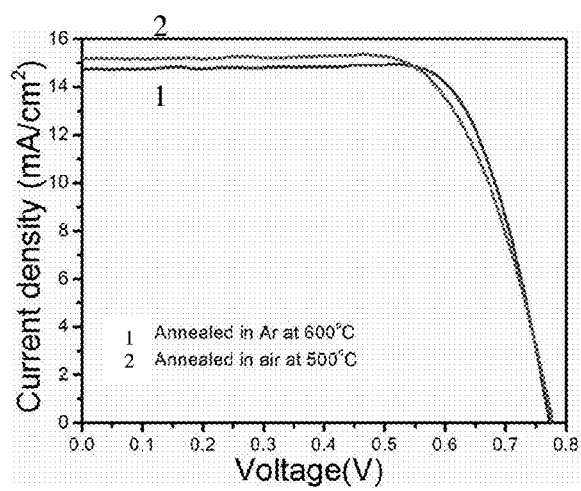
FIG. 11 is a graph showing the effect of annealing condition on device performance of DSSCs. I-V curves from DSSCs with only TiO$_2$ nanoparticles as photoanodes annealed at 600° C. in Ar (line 1) and at 500° C. in air (line 2) are shown.

To investigate the effect of SWNTs on efficient electron collection in photovoltaic devices, DSSCs were used as a model application due to their potential as a practical device and because their device physics is well understood. See, for example, O'Regan, B. & Gratzel, M. A low-cost, high-efficiency solar cell based on dye-sensitized colloidal $TiO_2$ films. *Nature* 353, 737-740 (1991); Chen, C.-Y. et al. Highly efficient light-harvesting ruthenium sensitizer for thin-film dye-sensitized solar cells. *ACS Nano* 3, 3103-3109 (2009); and Halme, J., et al., Device physics of dye solar cells. *Adv. Mater.* 22, E210-E234 (2010), each of which is incorporated by reference in its entirety. DSSCs with only $TiO_2$ nanoparticles as photoanodes were fabricated with the same method that other groups reported for easy comparison and used as a control. The SWNT/$TiO_2$ nanocomposites were mixed with $TiO_2$ nanoparticles (SWNT concentration in $TiO_2$ matrix varies from 0 to 0.2 wt %) and fabricated for DSSCs using the same method, except that the devices were annealed in an Ar atmosphere (instead of air) to protect SWNTs and elevated temperature (600° C. instead of 500° C.) to remove viruses and polymers. Control devices with only $TiO_2$ nanoparticles annealed at two different annealing conditions showed similar overall power conversion efficiencies, confirming the different annealing conditions used in this study did not affect the power conversion efficiency of DSSCs (FIG. 11). FIG. 1b shows device structures and photoelectrochemical processes in SWNT-incorporated DSSCs. In the photoelectrochemical process, $TiO_2$ nanoparticles accept electrons from photo-excited dyes, and these electrons are transferred to the conduction band of SWNTs after diffusion among $TiO_2$ nanoparticles. Then, SWNTs transport the electrons quickly to the current collector (fluorine doped tin oxide, FTO) to prevent back-electron transfer and recombination. In FIG. 3a, I-V curves show the photovoltaic performance of DSSCs with different electronic types of SWNTs incorporated into photoanodes. When pure semiconducting SWNTs (99% semiconducting components) were used, the short-circuit current ($I_{SC}$) increased by 27%, while pure metallic SWNTs (99% metallic components)-incorporated DSSC showed a decrease in $I_{SC}$ by 20% compared to $TiO_2$-only DSSCs. The fill factors were all approximately 0.7, and the open circuit voltages were all around 780 mV. Electron diffusion lengths of DSSCs were calculated from electrochemical impedance spectroscopy and shown in FIG. 3b. See, for example, Halme, J., et al., Device physics of dye solar cells. *Adv. Mater.* 22, E210-E234 (2010), which is incorporated by reference in its entirety. With semiconducting SWNTs, electron diffusion length increased, whereas electron diffusion length decreased with metallic SWNTs incorporated. Electron collection efficiencies of the devices were calculated from electron diffusion lengths and the different electron collection efficiencies account for the difference in the power conversion efficiencies. The electron collection efficiency was:

$$\eta_{COL} = \frac{\left[-L\alpha\cosh\left(\frac{d}{L}\right) + \sinh\left(\frac{d}{L}\right) + L\alpha e^{-\alpha d}\right]L\alpha}{(1 - e^{-\alpha d}) \cdot [1 - L^2\alpha^2]\cosh\left(\frac{d}{L}\right)}$$

where d is the thickness of the $TiO_2$ film, L is the electron diffusion length, $\alpha$ is the extinction coefficient of dye sensitized $TiO_2$ film. (L, here, was used for the thickness of the $TiO_2$ film and $L_n$ for the electron diffusion length.) For the calculation, it was assumed that $\alpha d$ equaled 1, indicating 90% of the incident light is absorbed. For semiconducting SWNTs incorporated DSSCs, L/d=8, $\eta_{COL}$=1; for DSSCs with only $TiO_2$ nanoparticles, L/d=2, $\eta_{COL}$=0.93; for metallic SWNTs incorporated DSSCs, L/d=0.5, $\eta_{COL}$=0.54 (all L/d values were taken at a bias value of 600 mV, as shown in FIG. 3b). Since the electron generation efficiency and charge separation efficiency are similar for the devices with different electronic types of SWNTs, the electron collection efficiency (decided by electron diffusion length) should fit to the difference of the power conversion efficiency. In fact, the calculated ratio of electron collection efficiency for semiconducting SWNTs incorporated DSSCs, DSSCs with only $TiO_2$ nanoparticles, and metallic SWNTs incorporated DSSCs is 1:0.93:0.54, and the measured power conversion efficiency ratio is 1:0.79:0.63. Thus, the order of magnitude differences in extrapolated diffusion length accounted for the difference in power conversion efficiency.

Therefore it was concluded that semiconducting or metallic SWNTs affect the device power efficiency differently by increasing or decreasing the electron diffusion length, and thus the short-circuit current. These opposing effects can be understood from the different electronic band structures of semiconducting and metallic SWNTs (FIG. 1c). Semiconducting SWNTs have a non-continuous band structure with a diameter-dependent bandgap. See, for example, Saito, R., et al., *Physical Properties of Carbon Nanotubes.* (Imperial College Press, London, 1998), which is incorporated by reference in its entirety. The electrons in the SWNT conduction band transferred from the $TiO_2$ conduction band can transport quickly to the FTO current collector without recombination or back reaction. On the contrary, metallic SWNTs (FIG. 1d) have a continuous band structure and therefore electrons transferred from $TiO_2$ can stay at a continuous energy level near the Fermi level, which accelerates recombination of electrons to the dye or back reaction to tri-iodide in the electrolyte. In FIGS. 1c-d, the dye absorbs photons and generates electron-hole pairs, and then instant charge separation occurs at the dye/$TiO_2$ interface preventing back electron transfer and charge recombination.

Figure 12:
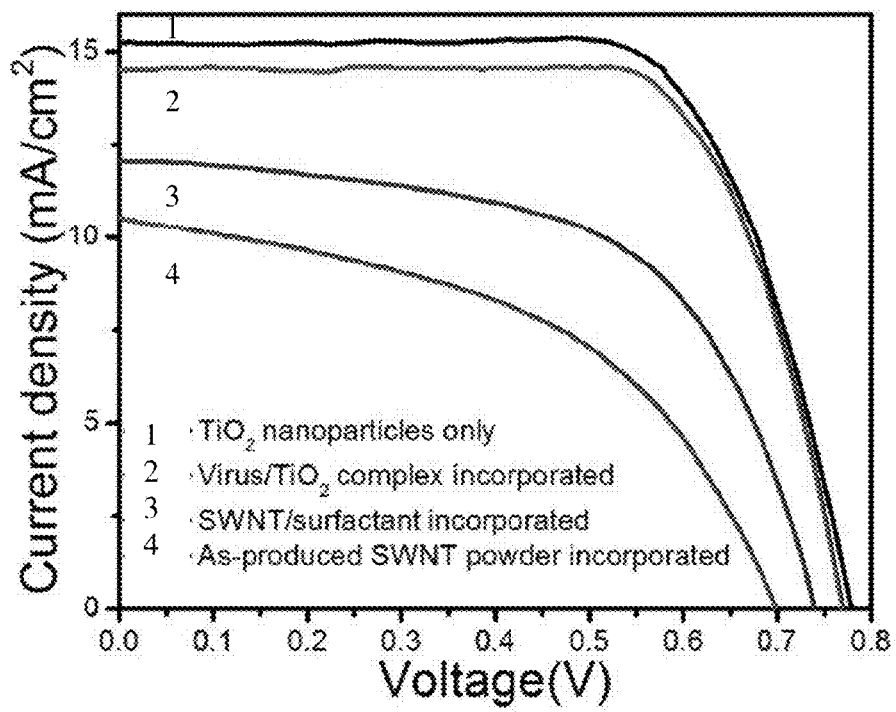
FIG. 12 is a graph showing the device performance of control DSSCs. Device performance of DSSCs with only TiO$_2$ nanoparticles (line 1), TiO$_2$ nanoparticles and virus/TiO$_2$ complex without SWNT (line 2), TiO$_2$ nanoparticles with surfactant-stabilized SWNT (line 3), and TiO$_2$ nanoparticles with as-produced SWNT powders (line 4).

The importance of the virus-SWNT template for synthesizing the SWNT/$TiO_2$ complexes and incorporating them into DSSCs was demonstrated by following control experiments. DSSCs with viruses but without SWNTs were shown to have similar device performance to the devices made with only $TiO_2$ nanoparticles (FIG. 12). This control experiment showed that the viruses did not participate in the photoelectrochemical processes (it is worth noting that here the template was only about 10% mass of the total $TiO_2$) and one-dimensional morphology of $TiO_2$ templated on the virus did not affect the performance of the device significantly. In fact, viruses bound SWNTs, prevented SWNTs from bundling, and acted as templates for assembling and synthesizing SWNT/$TiO_2$ core-shell nanocomposites by heterogeneous nucleation. Another control experiment using surfactant-stabilized SWNTs showed lower device efficiency (FIG. 12). Free surfactants in solution favored homogeneous nucleation as opposed to the heterogeneous nucleation for the encapsulation of SWNTs in $TiO_2$ when using virus-stabilized SWNTs. Homogeneous nucleation of $TiO_2$ resulted in SWNTs with exposed surfaces (bundles of SWNTs appeared after synthesis), increasing electron recombination and back reaction in DSSCs. Additionally, more surfactants than viruses were used to stabilize SWNTs, resulting in more impurities in the devices. Decreased efficiencies induced by bundling and impurities were also observed in control experiments in which as-produced SWNTs without surfactants were used (FIG. 12). Therefore, the combination of debundling of SWNTs and compact SWNT/$TiO_2$ nanocomposites enabled by a virus template, unique to this approach, was critical in investigating the effect of electronic type of SWNTs on device performance.

To optimize the electron collection, concentration dependence of power conversion efficiency was studied. Various concentrations from 0 to 0.2 wt % of SWNTs with different compositions of semiconducting and metallic components were incorporated into DSSCs. DSSCs incorporated with the pure semiconducting SWNTs showed continuous increases of efficiency, followed by saturation (from 8.3% for devices with only $TiO_2$ nanoparticles to 10.3% for devices with 0.2 wt % SWNT), as shown in FIG. 3c. L is the film thickness and $L_n$ is the electron diffusion length. The increase of the power efficiency was mainly due to the increased photocurrent. One possible explanation for the efficiency saturation could be that the number of SWNTs in the $TiO_2$ matrix was sufficient for electrons to transfer quickly from $TiO_2$ to SWNT (approximate calculations showed that electrons can transfer from $TiO_2$ to SWNTs after several hops with a typical 0.1 wt % SWNTs in $TiO_2$ nanoparticles matrix). When using SWNTs with more metallic components, however, the concentration dependence of the device efficiencies varied from having an optimized value with CoMoCAT SWNTs (about 10% metallic components) to a monotonic decrease with Hipco SWNTs (about 33% metallic components) and pure metallic SWNTs (about 99% metallic components). Although there have been reports on using other carbon-based nanomaterials for photovoltaic devices, for example, MWNTs, mixed semiconducting and metallic SWNTs and most recently graphene, there has been no report explicitly showing the opposing effects of pure metallic and semiconducting SWNTs on photovoltaic device performance. See, for example, Lee, K.-M., et al., Incorporating carbon nanotube in a low-temperature fabrication process for dye-sensitized $TiO_2$ solar cells. *Sol. Energy Mater. Sol. Cells* 92, 1628-1633 (2008); Kongkanand, A., et al., Single wall carbon nanotube scaffolds for photoelectrochemical solar cells. capture and transport of photogenerated electrons. *Nano Lett.* 7, 676-680 (2007); Brown, P., et al., Single-walled carbon nanotube scaffolds for dye-sensitized solar cells. *J. Phys. Chem. C* 112, 4776-4782 (2008); Tang, Y.-B. et al. Incorporation of graphenes in nanostructured $TiO_2$ films via molecular grafting for dye-sensitized solar cell application. *ACS Nano* 4, 3482-3488 (2010); Yang, N. et al. Two-dimensional graphene bridges enhanced photoinduced charge transport in dye-sensitized solar cells. *ACS Nano* 4, 887-894 (2010); and Ng, Y. H. et al. To what extent do graphene scaffolds improve the photovoltaic and photocatalytic response of $TiO_2$ nanostructured films? *J. Phys. Chem. Lett.* 1, 2222-2227 (2010), each of which is incorporated by reference in its entirety. Differences between results described herein and those from other researchers could be attributed to the following explanations. First, the efficiencies of the devices with only $TiO_2$ nanoparticles demonstrated here were relatively high (shown in FIG. 3a), implying that the recombination and back reaction were not severe, therefore the devices were more sensitive to additional metallic components. Second, well dispersed SWNTs and compact $SWNT/TiO_2$ nanocomposites allowed systematic investigation of the effects of semiconducting and metallic components separately. Third, annealing the devices at 600° C. in Ar gas ensured better contact between the SWNTs and $TiO_2$ and prevented SWNT loss in final devices.

Figure 13:
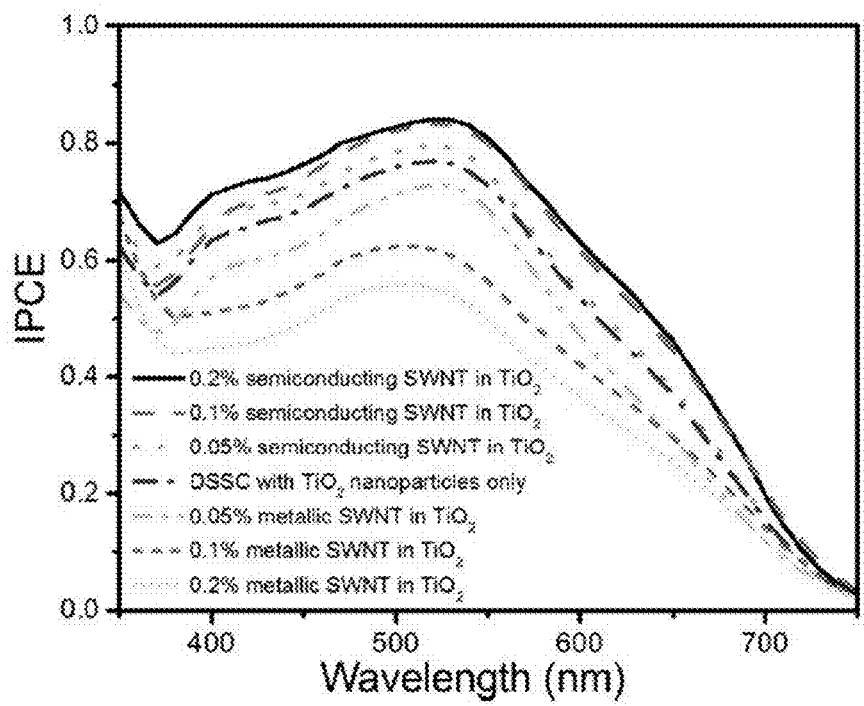
FIG. 13 is a graph showing IPCE measured for various DSSCs. DSSCs with only TiO$_2$ nanoparticles and with different SWNTs of various concentrations are compared.

Since SWNTs also absorb visible light, the possible effect of optical loss from SWNTs on device performance was investigated. The spectral response of IPCE for DSSCs with and without SWNTs and SWNTs of different electronic types and concentrations were measured. IPCE of different devices did not show significant changes in the spectral shape (FIG. 13). IPCE spectra were measured with a commercial IPCE measurement system (Model QEX7, PV Measurements, Inc.). Under full computer control, light from a xenon arc lamp was focused through a grating monochromator equipped with two 1200 grating lines/mm diffraction gratings onto the photovoltaic cell under test. The monochromator was incremented through the visible spectrum (from 350 nm to 750 nm) to generate the spectral response of IPCE with a spectral resolution of 10 nm. The incident photon flux was determined using a calibrated silicon photodiode (calibrated by PV Measurements, Inc.). Measurements were performed in a short-circuit condition while the cell was under background illumination from a bias light of 50 mW/cm². Bias illumination was from the same direction as the monochromatic light, which was from the FTO side. The monochromatic beam was chopped using a computer controlled shutter at a frequency of 4 Hz and averaging of up to 40 shutter cycles was employed.

Figure 14:
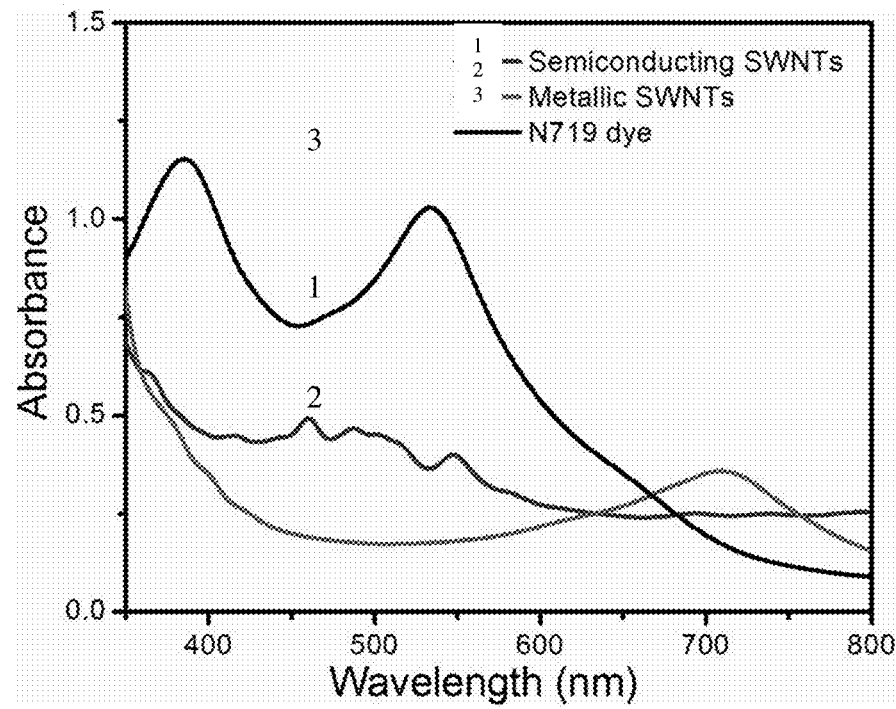
FIG. 14 is a spectra showing the comparison of absorption spectra from SWNTs and N719 dye in the visible region.

As shown in FIG. 14, the maximal absorption wavelength of metallic SWNTs in the visible region was around 700 nm, which did not overlap with the absorption peaks of N719 dye. As a result, the optical loss from metallic SWNTs did not affect the spectral shape of IPCE. The maximal absorption wavelength of semiconducting SWNTs in the visible region was around 500 nm and this range overlapped with the absorption peak of N719 dye (FIG. 14). The concentrations of measured solutions were not scaled with the final concentration used in the DSSCs to show the spectral difference more effectively. The concentration of semiconducting and metallic SWNTs aqueous solution was 10 μg/mL, and the concentration of N719 dye in the solution of acentonitrile/tert-butyl alcohol (volume ratio 1:1) was $5 \times 10^{-5}$ M. If the optical loss from semiconducting SWNTs affected the device performance, then the spectral response of IPCE around 500 nm would decrease with increasing concentrations of semiconducting SWNTs. However, IPCE for semiconducting SWNTs incorporated devices did not show significant difference around 500 nm. This indicated that optical loss from semiconducting SWNTs was not severe and did not affect the spectral shape of IPCE. The optical loss from low concentrations of SWNTs may not have contributed to the device performance significantly, and the different device performances might have arisen from different electron collection efficiencies.

The estimated optical loss from SWNTs in the devices was small, as calculated below. Assuming that N719 dye absorbed 90% of incident light (the transmission is 10%) in the absence of SWNTs, therefore the absorbance of N719 dye was 1 (Absorbance=−log(Transmission)). Also assuming that SWNTs absorb 10% of the incident light (the transmission is 90%) in the absence of N719, then the absorbance of SWNTs was 0.046. Combining N719 dye and SWNTs together in the devices, the overall absorbance was 1.046, and 91% (1-10$^{-Abs}$=10-1.046=0.91) of incident light was absorbed by N719 dye and SWNTs together. The light absorbed by them separately was 87% for N719 dye (91%×Abs(N719)/Abs(overall) =91%×1/(1+0.046)) and 4% for SWNTs (91%×Abs (SWNTs)/Abs(overall)=91%×0.046/(1+0.046)). Thus, the actual optical losses from SWNTs were about 3% of incident light (90%−87%=3%) at the maximal absorption wavelength of SWNTs. (If N719 dye absorbed 99% of incident light in absence of SWNTs, the calculated result of optical losses from SWNTs would be 2%.) Integrating the entire visible wavelength range, the effects of optical losses from SWNTs should be much less. (The assumption on the transmission and the absorbance of SWNTs is valid for 0.1 wt % SWNTs: the mass/volume concentration for 0.1 wt % SWNTs in $TiO_2$ is about 200 μg/cm³ considering that the density of $TiO_2$ is about 4 g/cm³ and the porosity of $TiO_2$ film is estimated as 0.5. Approximating the optical length for SWNTs in $TiO_2$ at 50 μm (considering the scattering effect of nanoporous $TiO_2$), then the absorbance of SWNTs is 0.05 μg$^{-1}$ cm$^{-2}$×200 μg$^{-1}$ cm$^{-3}$×50 μm=0.05.)

Effect of the Degree of Bundling on Photovoltaic Device Performance

The observed effects of semiconducting SWNTs and metallic SWNTs on the device performance motivated further tuning of the degree of bundling of SWNTs with the virus. To investigate the effect of bundling of SWNTs on the device performance, virus-SWNT complexes with virus-to-SWNT ratios of 1:2.5, 1:5, and 1:10 were made. Since the PL spectrum is more sensitive to bundle formation than the absorption spectrum, the PL spectra of the complexes were used to analyze degree of bundling of the complexes first. See, for example, O'Connell, M. J. et al. Band gap fluorescence from individual single-walled carbon nanotubes. *Science* 297, 593-596 (2002), which is incorporated by reference in its entirety. PL from SWNTs was measured with a home-built near-infrared (NIR) PL microscope. An inverted microscope was coupled to a Princeton Instruments OMA V 1D InGaAs array detector through a PI Acton SP2500 spectrometer. As excitation sources, a 785 nm laser and a Xe lamp coupled to a monochromator were used for PL spectra and PLE mapping, respectively.

Figure 4:
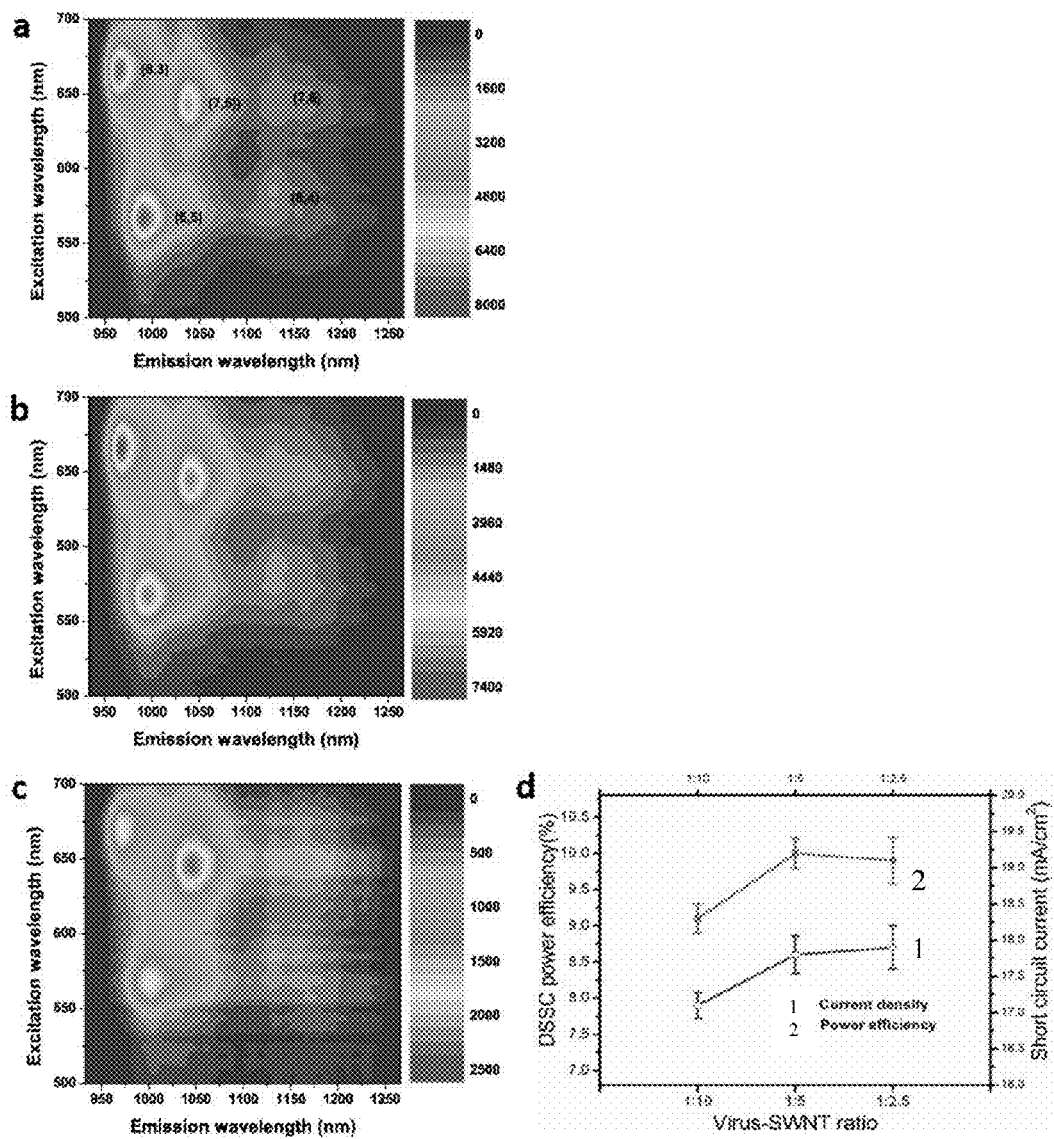
FIG. 4 are PLE maps of virus-SWNT complexes with virus-to-SWNT ratios of (a) 1:2.5; (b) 1:5; and (c) 1:10.

Because all the starting SWNT solutions used for the complexation were from the same batch and at the same concentration, the change of PL intensity was directly related to the degree of bundling of SWNTs. Results showed that the integrated PL intensity (between about 930 nm and about 1,250 nm) of the 1:10 sample was 5 times smaller compared to the 1:2.5 sample whereas the 1:5 sample was only 1.67 times smaller (FIG. 15). The integrated PL intensity (between about 935 nm and about 1,250 nm) of the 1:1 complex was 82% of the starting SWNTs in 2 wt % SC aqueous solution. This high quantum yield of the virus-SWNT complexes suggested that the developed virus-SWNT complexation method is an efficient way of dispersing SWNTs in aqueous solution. CoMoCAT SWNTs were used for the complexation. The lowest PL intensity of the 1:10 sample implied a relatively more bundled state of the 1:10 sample than either the 1:2.5 or the 1:5 sample. The more severe bundling of SWNTs in the 1:10 sample was further confirmed by the PL excitation (PLE) map. In the PLE map of the 1:10 sample, the relative PL intensity of (7,5) chirality was higher than both (8,3) and (6,5) chiralities, which was the opposite in the PLE maps of the 1:2.5 and the 1:5 sample as shown in FIGS. 4a, 4b, and 4c. In bundled SWNTs, in addition to the quenching of PL, excitons in the larger bandgap SWNT 'donors', can be transferred to smaller bandgap SWNT 'acceptors', and radiatively recombine to produce photons of lower energy. See, for example, Tan, P. H. et al. Photoluminescence spectroscopy of carbon nanotube bundles: evidence for exciton energy transfer. *Phys. Rev. Lett.* 99, 137402 (2007) and Han, J.-H. et al. Exciton antennas and concentrators from core-shell and corrugated carbon nanotube filaments of homogeneous composition. *Nature Mater.* 9, 833-839 (2010), each of which is incorporated by reference in its entirety. Therefore, the reverse of relative PL intensity of (7,5) in 1:10 sample can be explained as exciton energy transfer (EET) from donor (8,3) SWNT to acceptor (7,5) SWNT. The PLE mapping results showed the similar tendency of degree of bundling as PL spectra. CoMoCAT SWNTs were used for the complextion. CoMoCAT SWNTs are used with the concentration of 0.1 wt % in DSSCs.

Figure 5:
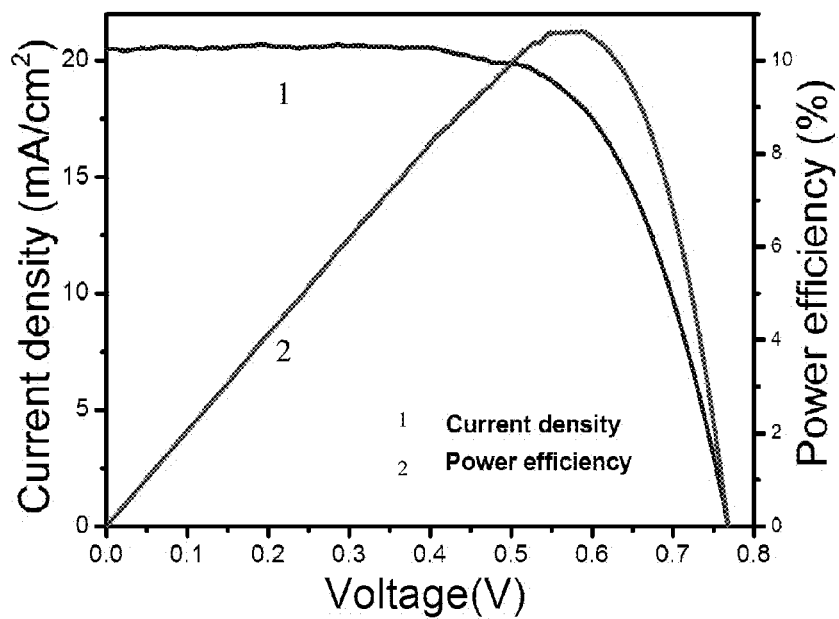
FIG. 5 is a graph showing the current density and power efficiency versus voltage curves of the DSSC with 0.1 wt % SWNT of 99% semiconducting component incorporated ((6, 5) chirality-enriched SWNT).

Complexes with different virus-to-SWNT ratios of 1:2.5, 1:5, and 1:10 were fabricated into DSSCs. The devices with the most bundled SWNTs (virus-to-SWNT ratio of 1:10) hd the lowest power conversion efficiency, 9.1%, while devices with less bundled SWNTs (virus-to-SWNT ratios of 1:2.5 and 1:5) showed higher values, 9.9% and 10% (FIG. 4d). Therefore, the degree of bundling of SWNTs also played an important role in photovoltaic device performance. Moreover, the sample of 1:2.5 virus-SWNT gave a virus-SWNT complex two times denser than the 1:5 virus-SWNT in $TiO_2$ matrix for the same concentration of SWNT. Thus, tuning the degree of bundling of SWNTs can reduce the amount of incorporated SWNTs further. By optimizing the effect of electronic properties of SWNTs and the microstructure of the template, a non-trivial improvement of power efficiency of DSSCs from 8.3% to 10.6% was achieved by incorporating only 0.1 wt % SWNTs (FIG. 5). This 10.6% power conversion efficiency of DSSCs was the best result for any SWNT-incorporated photovoltaic devices.

A general and programmable method can include using a genetically engineered virus to template compact core-shell SWNT/nanocrystals nanocomposites. SWNTs can be stabilized without surfactants or surface modifications and their electronic properties can be preserved. With the developed biological template approach, well-dispersed semiconducting SWNTs can improve the power conversion efficiency of DSSCs up to a value of 10.6%. Metallic and semiconducting SWNTs can affect the device performance in the opposite way. Aggregation states of SWNTs can affect the device performance, leading to further studies incorporating SWNTs in photovoltaic devices more effectively.

Because SWNTs have good thermal conductivity in addition to high electron mobility, this approach might improve the stability of large DSSC modules. See, for example, Hone, J., et al., Thermal conductivity of single-walled carbon nanotubes. *Physical Review B* 59, R2514 (1999), which is incorporated by reference in its entirety. Moreover, biological engineering of multiple genes of the virus can extend this approach to creation of more complex structures. See, for example, Lee, Y. J. et al. Fabricating genetically engineered high-power lithium-ion batteries using multiple virus genes. *Science* 324, 1051-1055 (2009), which is incorporated by reference in its entirety. Though the route to DSSC improvement lies in the development of dyes with absorption extending into the infrared and better redox couples which allow for higher voltages, the approach described herein can facilitate the utilization of SWNTs in many practical photovoltaic devices that require efficient electronic diffusion and reduced electron recombination, for instance, quantum dot solar cells, organic solar cells, and photoelectrochemical cells. See, for example, Mora-Seró, I. & Bisquert, J. Breakthroughs in the development of semiconductor-sensitized solar cells. *J. Phys. Chem. Lett.* 1, 3046-3052 (2010) and Arnold, M. S. et al. Sorting carbon nanotubes by electronic structure using density differentiation. *Nature Nanotech.* 1, 60-65 (2006), each of which is incorporated by reference in its entirety.

Other embodiments are within the scope of the following claims.

---

What is claimed is:

1. A method of making a photovoltaic device comprising:
providing a composition including a virus with binding affinity to nanotubes;
contacting the nanotubes to the virus, thereby forming a virus-nanotube complex;
adjusting the pH of the composition to a predetermined pH, thereby dispersing the nanotubes along the virus;
contacting a plurality of nanoparticles to the virus-nanotube complex, thereby forming a virus-nanotube-nanoparticle complex;
removing the virus from the virus-nanotube-nanoparticle complex, thereby forming a nanotube-nanoparticle complex; and
incorporating the nanotube-nanoparticle complex into a photovoltaic device,
wherein the nanotubes include semiconductive carbon nanotubes.

2. The method of claim 1, wherein the virus is a genetically engineered M13 virus.

3. The method of claim 1, wherein the plurality of nanoparticles includes inorganic nanoparticles.

4. The method of claim 1, wherein incorporating the nanotube-nanoparticle complex into a photovoltaic device includes forming a photoanode with the nanotube-nanoparticle complex.

5. The method of claim 1, wherein the photovoltaic device is a dye-sensitized solar cell.

* * * * *

SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 1

Asp Ser Pro His Thr Glu Leu Pro
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 2

Gly Leu Asn Glu Ile Phe Glu Ala Gln Lys Ile Glu Trp His Glu
1               5                   10                  15

```
<210> SEQ ID NO 3
<211> LENGTH: 68
<212> TYPE: DNA
<213> ORGANISM: Artificial Sequence
<220> FEATURE:
<223> OTHER INFORMATION: Synthetically generated primer

<400> SEQUENCE: 3
gtacctttct attctcactc tggcctgaac gacatcttcg aggctcagaa aatcgaatgg      60
cacgagtc                                                              68

<210> SEQ ID NO 4
<211> LENGTH: 68
<212> TYPE: DNA
<213> ORGANISM: Artificial Sequence
<220> FEATURE:
<223> OTHER INFORMATION: Synthetically generated primer

<400> SEQUENCE: 4
ggccgactcg tgccattcga ttttctgagc ctcgaagatg tcgttcaggc cagagtgaga      60
atagaaag                                                              68
```